US006855703B1

(12) United States Patent
Hill et al.

(10) Patent No.: US 6,855,703 B1
(45) Date of Patent: Feb. 15, 2005

(54) PHARMACEUTICAL COMPOSITIONS OF CONJUGATED ESTROGENS AND METHODS OF ANALYZING MIXTURES CONTAINING ESTROGENIC COMPOUNDS

(75) Inventors: Edward N. Hill, Wilmington, NC (US); Thomas W. Leonard, Wilmington, NC (US); Frederick D. Sancilio, Wilmington, NC (US); Katherin M. Schlipp, Wilmington, NC (US); Dean G. Shirazi, Wilmington, NC (US); Robert R. Whittle, Wilmington, NC (US)

(73) Assignee: Endeavor Pharmaceuticals, Wilmington, NC (US)

( * ) Notice: Subject to any disclaimer, the term of this patent is extended or adjusted under 35 U.S.C. 154(b) by 339 days.

(21) Appl. No.: 09/524,132

(22) Filed: Mar. 10, 2000

(51) Int. Cl.$^7$ .............................................. A61K 31/56

(52) U.S. Cl. ...................................................... 514/170

(58) Field of Search ......................................... 514/170

(56) References Cited

U.S. PATENT DOCUMENTS

| | | | |
|---|---|---|---|
| 3,230,142 A | 1/1966 | Spero ........................... 167/55 |
| 3,487,152 A | 12/1969 | Carstensen et al. .......... 424/240 |
| 3,502,772 A | 3/1970 | Ijzerman ...................... 424/239 |
| 3,568,828 A | 3/1971 | Lerner .......................... 206/42 |
| 3,591,688 A | 7/1971 | Jones et al. .................. 424/239 |
| 3,639,600 A | 2/1972 | Hendrix ....................... 424/242 |
| 3,733,407 A | 5/1973 | Segre ........................... 424/239 |
| 3,795,734 A | 3/1974 | Rochefort .................... 424/238 |
| 3,813,418 A | 5/1974 | Hofmeister et al. ....... 260/397.4 |
| 3,836,651 A | 9/1974 | Rudel et al. ................. 424/239 |
| 3,932,635 A | 1/1976 | Segre ........................... 424/239 |
| 3,939,264 A | 2/1976 | Lachnit-Fixson ............ 424/329 |
| 3,942,641 A | 3/1976 | Segre ........................... 206/534 |
| 3,957,982 A | 5/1976 | Lachnit-Fixson et al. ... 424/238 |
| 3,969,502 A | 7/1976 | Lachnit-Fixson ........... 424/239 |
| 4,027,019 A | 5/1977 | Shroff .......................... 424/238 |
| 4,066,757 A | 1/1978 | Pasquale ...................... 424/243 |
| 4,071,623 A | 1/1978 | van der Vies ............... 424/238 |
| 4,145,416 A | 3/1979 | Lachnit-Fixson et al. ... 424/238 |
| 4,147,783 A | 4/1979 | van der Vies ............... 424/243 |
| 4,154,820 A | 5/1979 | Simoons ...................... 424/175 |
| 4,210,644 A | 7/1980 | Ewing et al. ................ 424/239 |
| 4,259,325 A | 3/1981 | Prezewowsky et al. ..... 424/238 |
| 4,291,028 A | 9/1981 | Vorys ........................... 424/238 |
| 4,292,315 A | 9/1981 | Vorys ........................... 424/240 |
| 4,315,925 A | 2/1982 | Hussain et al. .............. 424/239 |
| 4,327,725 A | 5/1982 | Cortese et al. .............. 128/260 |
| 4,378,356 A | 3/1983 | De Jager ..................... 424/238 |
| 4,383,993 A | 5/1983 | Hussain et al. .............. 424/239 |
| 4,390,531 A | 6/1983 | Edgren ......................... 424/239 |
| 4,425,339 A | 1/1984 | Pitchford .................... 424/239 |
| 4,512,986 A | 4/1985 | Reel et al. ................... 514/170 |
| 4,530,839 A | 7/1985 | Pasquale ...................... 514/171 |
| 4,544,554 A | 10/1985 | Pasquale ...................... 514/170 |
| 4,616,006 A | 10/1986 | Pasquale ...................... 514/170 |
| 4,621,079 A | 11/1986 | Lachnit-Fixson et al. ... 514/170 |
| 4,628,051 A | 12/1986 | Pasquale ...................... 514/170 |
| 4,738,957 A | 4/1988 | Laurent et al. .............. 514/182 |
| 4,756,907 A | 7/1988 | Beck et al. .................... 424/85 |
| 4,762,717 A | 8/1988 | Crowley, Jr. ................ 424/425 |
| 4,764,378 A | 8/1988 | Keith et al. ................. 424/435 |
| 4,783,337 A | 11/1988 | Wong et al. ................. 424/468 |
| 4,816,257 A | 3/1989 | Buster et al. ................ 424/430 |
| 4,816,258 A | 3/1989 | Nedberge et al. ........... 424/448 |
| 4,826,831 A | 5/1989 | Plunkett et al. ............. 514/170 |
| 4,855,305 A | 8/1989 | Cohen .......................... 514/171 |
| 4,900,734 A | 2/1990 | Maxson et al. .............. 514/171 |
| 4,914,089 A | 4/1990 | Tax .............................. 514/170 |
| 4,921,843 A | 5/1990 | Pasquale ...................... 514/170 |
| 4,962,098 A | 10/1990 | Boissonneault ............. 514/170 |
| 4,977,147 A | 12/1990 | Jungblut et al. ............. 514/171 |
| 5,006,345 A | 4/1991 | Lang ........................... 424/467 |
| 5,010,070 A | 4/1991 | Boissonneault ............. 514/171 |

(List continued on next page.)

FOREIGN PATENT DOCUMENTS

| | | | | |
|---|---|---|---|---|
| DE | 2431694 A1 | 3/1976 | | |
| DE | 2624025 A1 | 12/1976 | | |
| DE | 3341638 A1 | 11/1983 | | |
| EP | 0322020 A1 | 6/1989 | ......... A61K/31/565 |
| GB | 1214712 | 12/1970 | | |
| GB | 1561244 | 2/1980 | | |
| GB | 2096462 A | 10/1982 | | |
| IL | 25265 | 12/1969 | | |
| WO | WO96/07416 | 3/1996 | .......... A61K/31/56 |
| WO | WO97/04752 | 2/1997 | .......... A61K/31/56 |

OTHER PUBLICATIONS

Townsend et al., J. of Chromatography, 450: 414–419, 1988.*
Memorandum, Center for Drug Evaluation and Research, May 5, 1997.*
PDR, 46: 2504–2518, 1992.*
Sakac, Marija N. et al., "Synthesis of New Steroidal N–butyl–N–methyl–undecanamide Derivatives," *Database Chemabs 'Online!*, Database accession No. 133:335378 XP002171995, ZB. Matice SRP. Prir. Nauke 96: 5–9 (1999).

(List continued on next page.)

*Primary Examiner*—Barbara P. Badio
(74) *Attorney, Agent, or Firm*—Myers Bigel Sibley & Sajovec, P.A.

(57) ABSTRACT

A composition of matter is provided having a mixture of active estrogenic compounds. The mixture is present in chemically pure form. The mixture includes salts of conjugated estrone, conjugated equilin, conjugated $\Delta^{8,9}$-dehydroestrone, conjugated 17α-estradiol, conjugated 17α-dihydroequilin, conjugated 17β-dihydroequilin, conjugated 17β-estradiol, conjugated equilenin, conjugated 17α-dihydroequilenin, and conjugated 17β-dihydroequilenin. The mixture also contains the same essential estrogenic compounds present in naturally derived equine conjugated estrogens. Drug products including the composition of matter are also provided, as are methods of using these drug products to treat mammals in need of treatment. Methods of analyzing mixtures containing conjugated estrogens are also provided.

44 Claims, 2 Drawing Sheets

U.S. PATENT DOCUMENTS

| | | | |
|---|---|---|---|
| 5,043,331 A | 8/1991 | Hirvonen et al. | 514/170 |
| 5,089,482 A | 2/1992 | Hermens et al. | 514/58 |
| 5,098,714 A | 3/1992 | Wright et al. | 424/473 |
| 5,108,995 A | 4/1992 | Casper | 514/170 |
| 5,130,137 A | 7/1992 | Crowley, Jr. | 424/422 |
| 5,183,814 A | 2/1993 | Dukes | 514/171 |
| 5,200,197 A | 4/1993 | Wright et al. | 424/473 |
| 5,208,225 A | 5/1993 | Boissonneault et al. | 514/178 |
| 5,210,081 A | 5/1993 | Raveendranath et al. | 514/179 |
| 5,262,408 A | 11/1993 | Bergink | 514/182 |
| 5,276,022 A | 1/1994 | Casper | 514/170 |
| 5,280,023 A | 1/1994 | Ehrlich et al. | 514/177 |
| 5,288,717 A | 2/1994 | Raveendranath et al. | 514/179 |
| 5,362,720 A | 11/1994 | Labrie | 514/169 |
| 5,382,573 A | 1/1995 | Casper | 514/170 |
| 5,418,228 A | 5/1995 | Bennink | 514/182 |
| 5,434,146 A | 7/1995 | Labrie et al. | 514/169 |
| 5,510,342 A | 4/1996 | Washburn et al. | 514/179 |
| 5,541,172 A | 7/1996 | Labrie | 514/169 |
| 5,545,634 A | 8/1996 | Labrie | 514/169 |
| 5,547,948 A | 8/1996 | Barcomb | 514/170 |
| 5,567,695 A | 10/1996 | Labrie | 514/169 |
| 5,629,303 A | 5/1997 | Labrie et al. | 514/169 |
| 5,654,011 A | 8/1997 | Jackson et al. | 424/635 |
| 5,753,639 A | 5/1998 | Labrie | 514/169 |
| 5,759,576 A | 6/1998 | Barcomb | 424/479 |
| 5,759,577 A | 6/1998 | Barcomb | 424/479 |
| 5,807,586 A | 9/1998 | Jackson et al. | 424/630 |
| 5,846,960 A | 12/1998 | Labrie | 514/169 |
| 5,861,387 A | 1/1999 | Labrie et al. | 514/169 |
| 5,861,431 A | 1/1999 | Hildebrand et al. | 514/557 |
| 5,908,638 A | 6/1999 | Huber et al. | 424/465 |
| RE36,247 E | 7/1999 | Plunkett et al. | 514/170 |
| 6,040,333 A | 3/2000 | Jackson | 514/456 |

OTHER PUBLICATIONS

Sakac, Marijan N. et al., "Chemical Behavior of 3,17.beta.–dipropionoxy–9.alpha.–hydroxyestra–1,3,5(10)–trien–6–one," *Database Chemabs 'Online!*, Database accession No. 128:180573 XP002171996, J. Serb. Chem. Soc., 63(1): 21–24 (1998).

Wiese, Thomas et al., "Induction of the Estrogen Specific Mitogenic Response of MCF–7 Cells by Selected Analogues of Estradiol–17β: A 3D Study," *Journal of Medicinal Chemistry*, 40(22): 3659–3669 (1997).

Yang et al., "The Hydroxylation and Amidation of Equilenin Acetate Catalyzed by Chloro[5,10,15,20–tetrakis(pentafluorophenyl)porphyrinato]managanese(III)," *Chem. Commun.*, 7: 531–532 (2000).

Rzheznikov, V.M. et al., "Synthesis and Biological Activity of Estrone 8–iso– and and D–homoanalogs Oxidized for Rings B and C," *Database Chemabs 'Online!*, Database accession No. 110:108353 XP002171997, Khim.–Farm. Zh. 22(12): 1462–1465 (1988).

Yang, Jerry et al., "Regioselective Oxidations of Equilenin Derivatives Catalyzed by a Phodium(III) Porphyrin Complex–Contrast with the Manganese(III) Porphyrin," *Tetrahedron Letters*, 41(42): 8063–8067 (2000).

Andreolini, et al., *Estrogen Conjugates in Late–Pregnancy Fluids: Extraction and Group Separation by a Graphitized Carbon Black Cartridge and Quantification by High–Performance Liquid Chromatography*, Anal. Chem. 59:1720–1725 (1987).

Fujino, et al., *3–(Difuoro–1,3,5–trianinyl)–1–(ethylthio)–2–n–propylbenz[f]isoindole as a Fluorescence Derivation Reagent for Estrogens in High–Performance Liquid Chromatography*, Chem. Pharm. Bull., 37(7): 1939–1940 (1989).

Vest, Floyd B. & Karnes, H. Thomas, *Luminescent Derivation of Estrogens for HPLC Detection* (Abstract), Department of Pharmacy and Pharmaceutics, Medical College of Virginia, APQ 1198.

Takadate, et al., *A Convenient Derivatization with Anion Exchange Resin Catalysts for High–Performance Liquid Chromatographic Analysis. I. Derivatization of Estrogens with Dansyl Chloride*, Chem. Pharm. Bull., 33(11): 5092–5095 (1985).

Novakovic, et al., *High–Performance Liquid Chromatographic Determination of Equine Estrogens with Ultraviolet Absorbance and Electrochemical Detection*, Journal of Chromatography A, 678: 359–363 (1994).

Townsend, et al., *High–Performance Liquid Chromatographic Determination of Conjugated Estrogens in Tablets*, Journal of Chromatography, 450: 414–419 (1988).

Ishida, et al., *Determination of Oestrogens in Pregnancy Urine by High–Performance Liquid Chromatography with Fluorescence Detection*, Journal of Chromatography, 431: 249–257 (1988).

*Conjugated Estrogens*, The United States Pharmacopeia (USP), published by United States Pharmacopeial Convention, Inc., pp. 627–629 (2000).

Synthetic Generic Conjugated Estrogens: Timeline, May 5, 1997, <http://www.fda.gov/cder/news/cetimeline.htm>.

FDA Statement on Generic Premarins, HHS News Press Release, P97–12, May 5, 1997, <http://www.fda.gov/cder/cepressrelease.htm>.

New Drug Approval for Cenestin, Synthetic Conjugated Estrogens, A: Mar. 24, 1999, *Questions and Answers*, <http://www.fda.gov/cder/news/cenestin/qa.htm>.

NDA 20–992 Cenestin™ (synthetic conjugated estrogens, A) Tablets Physicians Package Insert, pp. 1–10 (1999).

NDA 20–992 Cenestin™ (synthetic conjugated estrogens, A) Tablets Patient Package Insert, pp. 11–13 (1999).

FDA Backgrounder on Conjugated Estrogens, May 5, 1997, <http://www.fda.gov/cder/cebackground.htm>.

Letter from Yana Ruth Mille, Chief, Compendial Operations Staff, HFD–354, Office of Pharmaceutical Science, Center for Drug Evaluation & Research to Joseph G. Valentino, J.D., Senior Vice President and General Counsel, The United States Pharmacopeial Convention, Inc. (Mar. 8, 2000)(REF: 3–00–001–O), (REF: 3–00–002–O).

Memorandum from Janet Woodcock, M.D., Director, Center for Drug Evaluation & Research to Douglas L. Sporn, Director, Office of Generic Drugs, regarding Approvability of a Synthetic Generic Version of Premarin (May 5, 1997).

Center for Drug Evaluation and Research (CDER),Guidance for Industry, Draft Guidance, *Conjugated Estrogens, USP—LC–MS Method for Both Qualitative Chemical Characterization and Documentation of Qualitative Pharmaceutical Equivalence*, Mar. 2000, <http://www.fda.gov/cder/guidance/index.htm>.

Physician's Desk Reference, 53: 3367–3379 (1999).

Letter from Stuart J. Land, Donald O. Beers and David E. Korn, Arnold & Porter, and Nancy L. Buc, Buc & Beardsley to Dockets Management Branch, Food and Drug Administration, Department of Health and Human Services (May 12, 1998).

Letter from Gloria Ortega, Dockets Management Branch, Department of Health & Human Services to Stuart J. Land, Arnold & Porter (May 13, 1998).

Letter from Janet Woodcock, Director, Center for Drug Evaluation and Research to Stuart J. Land, Donald O. Beers and David E. Korn, Arnold & Porter and Nancy L. Buc, Buc & Beardsley (Mar. 24, 1999) (Doctet No.: 98P–0311/CPI).

S. Poole & C. Poole, "Separation of Pharmaceutically Important Estrogens by Micellar Electrokinetic Chromatography," *Journal of Chromatography A*, 749: 247–255 (1996).

Sj. Van Der Wal & J.F.K. Huber, "Comparative Study of Several Phase Systems for the Separation of Estrogen Conjugates by High–Pressure Liquid Chromatography," *Journal of Chromatography*, 149: 431–453 (1978).

\* cited by examiner

PHARMACEUTICAL COMPOSITIONS OF CONJUGATED ESTROGENS AND METHODS OF ANALYZING MIXTURES CONTAINING ESTROGENIC COMPOUNDS

FIELD OF THE INVENTION

The invention generally relates to pharmaceutical compositions exhibiting estrogenic activity, along with methods of administering and making the same.

BACKGROUND OF THE INVENTION

Pharmaceutical formulations containing conjugated-estrogens (e.g., Premarin® (conjugated estrogens, USP) made available commercially by Wyeth-Ayerst Laboratories of Philadelphia, Pa.) have long been used for moderate to severe vasomotor symptoms associated with menopause, atrophic vaginitis, osteoporosis, hypoestrogenism due to hypogonadism, castration, or primary ovarian failure, breast cancer in selected persons with metastatic disease, and advanced androgen-dependent carcinoma of the prostate. Premarine® (conjugated estrogens, USP) has been known to contain a mixture of estrogens obtained exclusively from natural sources, occurring as the sodium salts of water-soluble estrogen sulfates blended to represent the average composition of material derived from pregnant mares' urine. As Premarin® (conjugated estrogens, USP) is derived from the urine of pregnant mares, the methods utilized to collect this urine have recently come into question. Animal activists have begun to protest these methods and call for a ban on Premarin® (conjugated estrogens, USP) despite its apparent utility in treating the aforementioned diseases. Premarin® (conjugated estrogens, USP) is generally believed to contain a number of estrogenic compounds. However, despite numerous attempts to characterize Premarin® (conjugated estrogens, USP) over the past several decades, the essential estrogenic compounds present in Premarin® (conjugated estrogens, USP) have remained a mystery.

It would be desirable to obtain a synthetic conjugated estrogens formulation that contains the essential estrogenic compounds present in Premarin® (conjugated estrogens, USP).

Summary of the Invention

According to the present invention, the essential estrogenic compounds present in Premarin® (conjugated estrogens, USP) have been determined for the first time. These essential estrogenic compounds have been determined to consist of the salts of conjugated estrone, conjugated equilin, conjugated $\Delta^{8,9}$-dehydroestrone, conjugated 17α-estradiol, conjugated 17α-dihydroequilin, conjugated 17β-dihydroequilin, conjugated 17β-estradiol, conjugated equilenin, conjugated 17α-dihydroequilenin, and conjugated 17β-dihydroequilenin. While the sodium salts of the sulfate conjugates of the foregoing ten compounds have been listed as the estrogenic components of Premarin® (conjugated estrogens, USP), until now it has, not been known that the foregoing ten compounds are the only essential estrogenic compounds present in Premarin® (conjugated estrogens, USP). Without this knowledge, it has heretofore not been possible to formulate a chemically pure or synthetic mixture of estrogenic compounds that contains the same essential estrogenic compounds found in Premarin® (conjugated estrogens, USP).

In one aspect, the present invention provides a composition of matter. The composition of matter comprises a mixture of estrogenic compounds. The mixture may be present in chemically pure form. The mixture may include salts of conjugated estrone, conjugated equilin, conjugated $\Delta^{8,9}$-dehydroestrone, conjugated 17α-estradiol, conjugated 17α-dihydroequilin, conjugated 17β-dihydroequilin, conjugated 17β-estradiol, conjugated equilenin, conjugated 17α-dihydroequilenin, and conjugated 17β-dihydroequilenin. The mixture may include the same essential estrogenic compounds present in naturally derived equine conjugated estrogens.

According to embodiments of the present invention, the mixture may include the salts of estrone sulfate, equilin sulfate, $\Delta^{8,9}$-dehydroestrone sulfate, 1 7α-estradiol sulfate, 17α-dihydroequilin sulfate, 17β-dihydroequilin sulfate, 17β-estradiol sulfate, equilenin sulfate, 17α-dihydroequilenin sulfate, and 17β-dihydroequilenin sulfate.

According to other embodiments of the present invention, the mixture may include the sodium salts of conjugated estrone, conjugated equilin, conjugated $\Delta^{8,9}$-dehydroestrone, conjugated 17α-estradiol, conjugated 17α-dihydroequilin, conjugated 17β-dihydroequilin, conjugated 17β-estradiol, conjugated equilenin, conjugated 17α-dihydroequilenin, and conjugated 17β-dihydroequilenin.

According to still other embodiments of the present invention, the mixture may include the sodium salts of estrone sulfate, equilin sulfate, $\Delta^{8,9}$-dehydroestrone sulfate, 17α-estradiol sulfate, 17α-dihydroequilin sulfate, 17β-dihydroequilin sulfate, 17β-estradiol sulfate, equilenin sulfate, 17α-dihydroequilenin sulfate, and 17β-dihydroequilenin sulfate.

In another aspect, the invention provides a method of treating mammals in need of treatment. The method comprises administering an effective amount of a composition of matter. Examples of treatments that are addressed by the compositions of the invention include vasomotor symptoms, atrophic vaginitis, and osteoporosis.

In yet another aspect, the present invention provides a method of analyzing conjugated estrogen constituents. The method includes the steps of preparing a solution containing conjugated estrogens and analyzing the conjugated estrogens solution utilizing an HPLC system. The conjugated estrogens solution includes a mixture of conjugated estrogens, and a mobile phase having an organic portion that includes between about 0.1% and about 30% of a protic solvent by volume of organic portion and between about 70% and about 100% of a polar aprotic solvent by volume of organic portion, and an aqueous diluent.

The invention is described in greater detail with respect to the preferred embodiments set forth hereinbelow.

DETAILED DESCRIPTION OF THE PREFERRED EMBODIMENTS

Figure 1:
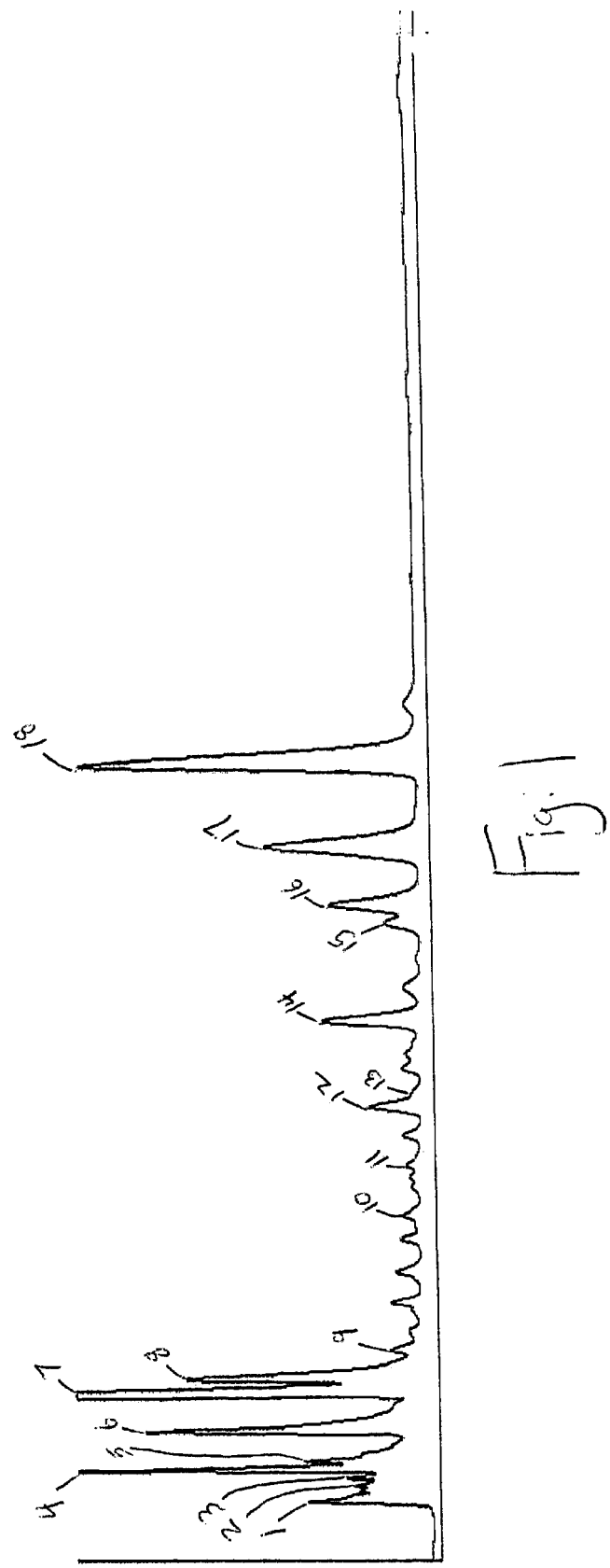
FIG. 1 is a chromatogram of Premarin® (conjugated estrogens tablets, USP) according to the prior art.

The invention will now be described with reference to the embodiments set forth herein. These embodiments are intended to illustrate the invention and are not meant to limit the scope of the invention, which is defined by the claims.

In one aspect, the invention relates to a composition of matter. The composition of matter comprises a mixture of estrogenic compounds. The mixture is present in chemically pure form and includes salts of conjugated estrone, conjugated equilin, conjugated $\Delta^{8,9}$-dehydroestrone, conjugated 17α-estradiol, conjugated 17α-dihydroequilin, conjugated 17β-dihydroequilin, conjugated 17β-estradiol, conjugated equilenin, conjugated 17α-dihydroequilenin, and conjugated 17β-dihydroequilenin. The mixture contains the same essential estrogenic compounds present in naturally derived equine conjugated estrogens. All of the essential estrogenic compounds may be combined as part of the mixture. Alternatively, a portion of the essential estrogenic compounds may be combined as part of the mixture and some or all of these or other compounds may degrade to some extent resulting in a mixture containing the same essential estrogenic compounds present in naturally derived equine conjugated estrogens.

For the purposes of the present invention, "naturally derived equine conjugated estrogens" may be defined as a drug product (i.e. Premarin® (conjugated estrogens tablets, USP)) containing a mixture of estrogens obtained exclusively from natural sources and blended to represent the average composition of material derived from pregnant mares' urine. "Essential estrogenic compounds" may be defined as estrogenic compounds that are consistent and controlled (i.e. less than +/−50% variation between lots), are present in concentrations >0.1% by weight of the mixture of estrogenic compounds, and have a chemical structure that has the potential to have a meaningful estrogenic activity (i.e. has a phenolic A ring (at carbon 3) and a β-hydroxyl or ketone group in position 17 of the D ring (see *Goodman and Gilman's The Pharmacological Basis of Therapeutics*, 1412 (9th ed., 1996))). As used herein, "chemically pure form" means substantially devoid of impurities present in naturally derived equine conjugated estrogens products, more preferably substantially devoid of indican, sulfated benzyl alcohol, hippuric acid, benzoic acid, and creatinine.

According to the present invention, the essential estrogenic compounds present in naturally derived equine conjugated estrogens have now been determined for the first time. These essential estrogenic compounds consist of the following 10 compounds, the salts of their conjugates, or mixtures thereof: estrone; equilin; $\Delta^{8,9}$-dehydroestrone; 17α-estradiol; 17α-dihydroequilin; 17β-dihydroequilin; 17β-estradiol; equilenin; 17α-dihydroequilenin; and 17β-dihydroequilenin. Preferably, the essential estrogenic compounds present in naturally derived equine conjugated estrogens consist of the sodium salts of the conjugates of estrone; equilin; $\Delta^{8,9}$-dehydroestrone; 17α-estradiol; 17α-dihydroequilin; 17β-dihydroequilin; 17β-estradiol; equilenin; 17α-dihydroequilenin; and 17β-dihydroequilenin. More preferably, the essential estrogenic compounds present in naturally derived equine conjugated estrogens consist of the sodium salts of estrone sulfate; equilin sulfate; $\Delta^{8,9}$-dehydroestrone sulfate; 17α-estradiol sulfate; 17α-dihydroequilin sulfate; 17β-dihydroequilin sulfate; 17β-estradiol sulfate; equilenin sulfate; 17α-dihydroequilenin sulfate; and 17β-dihydroequilenin sulfate.

In compositions of matter of the present invention, the estrogenic compounds may be present in various forms, including, but not limited to, estrogenic ketones and their corresponding 17α- and 17β-hydroxy derivatives. For example, the estrogenic compounds may include estrone, 17α-estradiol, 17β-estradiol, equilin, 17α-dihydroequilin, 17β-dihydroequilin, equilenin, 17α-dihydroequilenin, 17β-dihydroequilenin, $\Delta^{8,9}$-dehydroestrone, 17α$\Delta^{8,9}$-dehydroestradiol, 17β$\Delta^{8,9}$-dehydroestradiol, 6-OH equilenin, 6-OH 17α-dihydroequilenin, and 6-OH 17β-dihydroequilenin. The estrogenic compounds may also be present as conjugated estrogens. The conjugates may be various conjugates understood by those skilled in the art, including, but not limited to, glucuronide and sulfate. The most preferred conjugate is sulfate. The estrogenic compounds may also be present as salts of conjugated estrogens. The salts may be various salts understood by those skilled in the art, including, but not limited to, sodium salts, calcium salts, magnesium salts, lithium salts, and amine salts such as piperazine salts. The most preferred salts are sodium salts. A synthetic estrogenic compound may be defined as one that is derived or obtained from sources other than natural sources.

The mixture preferably comprises from about 40 to about 75 percent of an estrone compound, from about 15 to about 40 percent of an equilin compound, from about 2 to about 10 percent of a $\Delta^{8,9}$-dehydroestrone compound, from about 2 to about 10 percent of a 17α-estradiol compound, from about 10 to about 20 percent of a 17α-dihydroequilin compound, and from about 0.5 to about 5 percent of a 17β-dihydroequilin compound. The mixture preferably further comprises from about 0.05 to about 3.5 percent of a 17α-dihydroequilenin compound, from about 0.05 to about 3 percent of a 17β-dihydroequilenin compound, from about 0.05 to about 6 percent of a equilenin compound, and from about 0.05 to about 2.5 percent of a 17β-estradiol compound. The estrogen compounds are preferably present as salts of the conjugated compounds, most preferably sodium salts of the estrogen sulfates.

The sum percent of the estrone compound and the equilin compound preferably ranges from about 70 to about 95 percent, more preferably from about 75 to about 95 percent. The ratio of the percent of the equilin compound to percent of the estrone compound is preferably from about 0.25 to about 0.75, more preferably from about 0.3 to about 0.7, and most preferably from about 0.35 to about 0.65. As used herein when describing the mixture of estrogenic compounds, percent is to be understood to mean the percent by weight based on the labeled content of conjugated estrogens.

Estrogenic compounds and/or mixtures thereof are commercially available from various suppliers including Berlichem, Inc. of Montville, N.J.; Organics/Lagrange of Chicago, Ill.; and Diosynth, Inc. of Chicago, Ill.

In one embodiment, the composition of the invention may include at least one additional pharmaceutically active ingredient. Examples of additional active ingredients include, but are not limited to, androgens, progestins, calcium salts, and vitamin D and its derivatives such as calcitriol. Examples of androgens include, without limitation, methyltestosterone; fluoxymesterone; oxandrolone; oxymetholone; stanozolol; 7α-methyl-19-nortestosterone; testosterone; testosterone cypionate; testosterone enanthate; testosterone propionate; danazol; 5α-androstan-3α-ol-16-one; 5α-androstan-3β,16β-diol; 5α-androstan-3β,16α-diol; and 5α-androstan-3β,17α-diol. Examples of progestins are set forth in U.S. Patent No. Re. 36,247 to Plunkett et al., the disclosure of which is incorporated herein in its entirety. Examples include, but are not limited to, desogestrel; dydrogesterone; ethynodiol diacetate; medroxyprogesterone acetate; levonorgestrel; medroxyprogesterone acetate; hydroxyprogesterone caproate; norethindrone; norethindrone acetate; norethynodrel; allylestrenol; 19-nortestosterone; lynoestrenol; quingestanol acetate; medrogestone; norgestrienone; dimethisterone; ethisterone; cyproterone acetate; chlormadinone acetate; megestrol acetate; norgestimate; norgestrel; desogestrel; trimegestone; gestodene; nomegestrel acetate; progesterone; 5α-pregnan-3β,20α-diol sulfate; 5α-pregnan- 3β,20β-diol sulfate; 5α-pregnan-3β-ol-20-one; 16,5α-pregnen-3β-ol-20-one; and 4-pregnen-20β-ol-3-one-20-sulfate. Calcium salts may include, without limitation, organic acids salts of calcium such as calcium citrate, calcium lactate, calcium fumurate, calcium acetate, and calcium glycerophosphate, as well as inorganic salts such as calcium chloride, calcium phosphate, calcium sulphate, and calcium nitrate.

Pharmaceutically acceptable salts, solvates, hydrates, and polymorphs may be formed of any of the active ingredients employed in the composition of the invention. The invention also encompasses embodiments in which the composition of matter defined herein is included in various quantities in combination with known pharmaceutically accepted formulations. For example, the composition of matter of the invention may be incorporated into various known estrogen-containing drug products such as, Premarin® made commercially available by Wyeth-Ayerst Laboratories of Philadelphia, Pa. The composition of matter of the invention may also be employed as part of a continuous estrogen-progestogen therapy regimen such as that described by U.S. Patent No. Re. 36,247 to Plunkett et al. and is present commercially as Prempro® and Premphase® made available by Wyeth-Ayerst Laboratories, the disclosure of which is incorporated herein by reference in its entirety.

Figure 2:
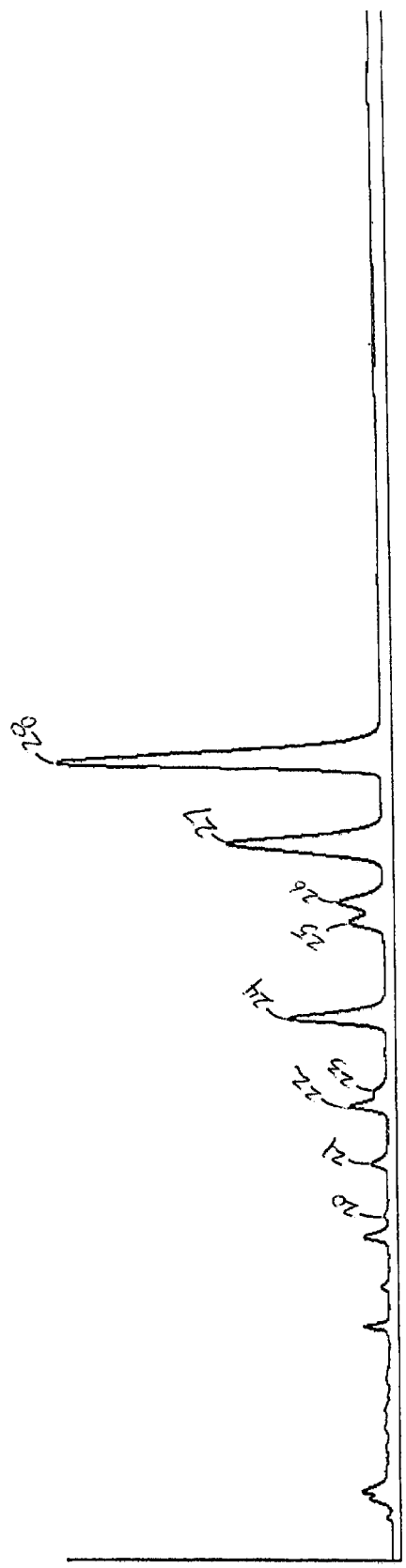
FIG. 2 is a chromatogram of an embodiment of a conjugated estrogens composition according to the present invention.

A preferred mixture of active estrogenic compounds of the present invention may be illustrated by the chromatogram of FIG. 2.

The present invention also encompasses pharmaceutically acceptable drug products comprising a composition of matter of the present invention and at least one pharmaceutically acceptable carrier, diluent, or excipient, the selection of which are known to the skilled artisan. The drug product formulations can be in the form of tablets; effervescent tablets; pills; powders; elixirs; suspensions; emulsions; solutions; syrups; soft and hard gelatin capsules; transdermal patches; topical gels, creams and the like; suppositories; sterile injectable solutions; and sterile packaged powders.

In certain embodiments, the drug product is present in a solid pharmaceutical composition that may be suitable for oral administration. A solid composition of matter according to the present invention may be formed and may be mixed with an excipient, diluted by an excipient or enclosed within such a carrier which can be in the form of a capsule, sachet, tablet, paper, or other container. When the excipient serves as a diluent, it may be a solid, semi-solid, or liquid material which acts as a vehicle, carrier, or medium for the composition of matter.

Various suitable excipients will be understood by those skilled in the art and may be found in the *National Formulary* 19, pages 2404–2406 (2000), the disclosure of pages 2404 to 2406 being incorporated herein in their entirety. For example, the drug product formulations may include lubricating agents such as, for example, talc, magnesium stearate and mineral oil; wetting agents; emulsifying and suspending agents; binding agents such as starches, gum arabic, microcrystalline cellulose, cellulose, methylcellulose, and syrup; anticaking agents such as calcium silicate; coating agents such as methacrylates and shellac; preserving agents such as methyl- and propyl hydroxybenzoates; sweetening agents; or flavoring agents. Polyols, buffers, and inert fillers may also be used. Examples of polyols include, but are not limited to, mannitol, sorbitol, xylitol, sucrose, maltose, glucose, lactose, dextrose, and the like. Suitable buffers encompass, but are not limited to, phosphate, citrate, tartarate, succinate, and the like. Other inert fillers which may be used encompass those which are known in the art and are useful in the manufacture of various dosage forms. If desired, the solid formulations may include other components such as bulking agents and/or granulating agents, and the like. The drug products of the invention may be formulated so as to provide quick, sustained, or delayed release of the active ingredient after administration to the patient by employing procedures well known in the art.

To form dosage units for oral administration, the composition of matter of the present invention may be mixed with a solid, pulverant carrier such as, for example, lactose, saccharose, sorbitol, mannitol, starch, amylopectin, cellulose derivatives or gelatin, as well as with an antifriction agent such as, for example, magnesium stearate, calcium stearate, and polyethylene glycol waxes. The mixture may then be pressed into tablets. Tablets for oral use may also be prepared in the following manner, although other techniques may be employed. The solid substances are ground or sieved to a desired particle size, and the binding agent is homogenized and suspended in a suitable solvent. The active ingredient and auxiliary agents are mixed with the binding agent solution. The resulting mixture is moistened to form a uniform suspension. The moistening typically causes the particles to aggregate slightly, and the resulting mass is pressed through a stainless steel sieve having a desired size. The layers of the mixture are then dried in controlled drying units for determined length of time to achieve a desired particle size and consistency. The granules of the dried mixture are sieved to remove any powder. To this mixture, disintegrating, anitfriction, and anti-adhesive agents are added. Finally, the mixture is pressed into tablets using a machine with the appropriate punches and dies to obtain the desired tablet size. The operating parameters of the machine may be selected by the skilled artisan.

If coated tablets are desired, the above prepared cores may be coated with a concentrated solution of sugar, which may contain gum arabic, gelatin, talc, titanium dioxide, or with a lacquer dissolved in volatile organic solvent or mixture of solvents. Additionally, coating may be carried out in aqueous or nonaqueous media using various excipients including, but not limited to, dispersed methylcellulose, dispersed ethylcellulose, dispersed methacrylates or mixtures thereof. To this coating various dyes may be added in order to distinguish among tablets with different active compounds or with different amounts of the active compound present. Additionally, active ingredients may be added to the coatings. In a particular embodiment, the active ingredient may be present in a core surrounded by one or more layers including sustained release coating layers.

Soft gelatin capsules may be prepared in which capsules contain a mixture of the active ingredient and vegetable oil. Hard gelatin capsules may contain granules of the active ingredient in combination with a solid, pulverulent carrier, such as, for example, lactose, saccharose, sorbitol, mannitol, potato starch, corn starch, amylopectin, cellulose derivatives, or gelatin.

In one preferred embodiment, the formulation is in the form of orally-administered tablets which contain the composition of matter of the present invention as set forth herein along with the following inactive ingredients: calcium phosphate tribasic, calcium sulfate, camauba wax, cellulose, glyceryl monooleate, lactose, magnesium stearate, methylcellulose, pharmaceutical glaze, polyethylene glycol, stearic acid, sucrose, and titanium dioxide. Such ingredients may be present in amounts similar to those present in Premarin® (conjugated estrogens tablets, USP) made commercially available by Wyeth-Ayerst Laboratories of Philadelphia, Pa. Tablets employing the active ingredients of the invention may contain excipients similar to those contained in the 0.3 mg., 0.625 mg., and 1.25 mg tablets of Premarin® (conjugated estrogens tablets, USP).

Liquid preparations for oral administration may be prepared in the form of syrups or suspensions, e.g., solutions containing an active ingredient, sugar, and a mixture of ethanol, water, glycerol, and propylene glycol. If desired, such liquid preparations may contain coloring agents, flavoring agents, and saccharin. Thickening agents such as carboxymethylcellulose may also be used.

In the event that the above formulations are to be used for parenteral administration, such a formulation may comprise sterile aqueous injection solutions, non-aqueous injection solutions, mixtures of aqueous and non-aqueous injection solutions, or dry sterile lyphilized cake for reconstitution comprising compositions of matter of the present invention. When aqueous injection solutions are prepared, the composition of matter may be present as a water soluble pharmaceutically acceptable salt. Parenteral preparations may contain anti-oxidants, buffers, bacteriostats, and solutes which render the formulation isotonic with the blood of the intended recipient. Aqueous and non-aqueous sterile suspensions may include suspending agents and thickening agents. The formulations may be presented in unit-dose or multi-dose containers, for example sealed ampules and vials. Extemporaneous injection solutions and suspensions may be prepared from sterile powders, granules and tablets of the kind previously described.

In a preferred embodiment, the drug product of the present invention is in the form of an injectable solution containing a predetermined amount (e.g., 25 mg) of the composition of matter in a sterile lyphilized cake which also contains lactose, sodium citrate, and simethicone. The pH of a solution containing the above ingredients may be adjusted using a suitable agent (e.g., sodium hydroxide or hydrochloric acid). Reconstitution may be carried out according to known methods, e.g., using a sterile diluent (5 mL) containing 2 percent benzyl alcohol in sterile water. A preferred injectable solution is similar to Premarin® Intravenous made commercially available by Wyeth-Ayerst Laboratories.

The composition of matter also may be formulated such that it is suitable for topical administration (e.g., vaginal cream). These formulations may contain various excipients known to those skilled in the art. Suitable excipients may include, but are not limited to, cetyl esters wax, cetyl alcohol, white wax, glyceryl monostearate, propylene glycol monostearate, methyl stearate, benzyl alcohol, sodium lauryl sulfate, glycerin, mineral oil, water, carbomer, ethyl alcohol, acrylate adhesives, polyisobutylene adhesives, and silicone adhesives.

In a preferred embodiment, the drug product is in the form of a vaginal cream containing the composition of matter as set forth herein present in a nonliquefying base. The nonliquefying base may contain various inactive ingredients such as, for example, cetyl esters wax, cetyl alcohol, white wax, glyceryl monostearate, propylene glycol monostearate, methyl stearate, benzyl alcohol, sodium lauryl sulfate, glycerin, and mineral oil. Such composition may be formulated similar to Premarin® Vaginal Cream made commercially available by Wyeth-Ayerst Laboratories.

Dosage units for rectal administration may be prepared in the form of suppositories which may contain the composition of matter in a mixture with a neutral fat base, or they may be prepared in the form of gelatin-rectal capsules which contain the active substance in a mixture with a vegetable oil or paraffin oil.

In another aspect, the present invention relates to methods of treating mammals (e.g., man) in need of treatment. The methods include administering an effective amount of a composition of matter as defined herein to the mammal in need of treatment. The methods may be used for a number of treatments such as, but not limited to, vasomotor symptoms; atrophic vaginitis; osteoporosis; hypoestrogenism due to hypogonadism, castration, or primary ovarian failure; breast cancer in selected persons with metastatic disease; advanced androgen-dependent carcinoma of the prostate; abnormal uterine bleeding; and kraurosis vulvae. The administration may be cyclic, occurring for one or more short periods of time or courses of treatment (i.e. short-term use). Alternatively, the administration may be continuous, occurring over extended periods of time (i.e. long-term use). One example of long-term use would be from the onset of menopause until death. Cyclic and continuous administration may be either interrupted or uninterrupted. Uninterrupted administration occurs one or more times daily such that there is no break in treatment. Interrupted administration occurs other than daily, for example a repeated course of treatment including three weeks of daily treatment followed by one week of no treatment.

In another aspect, the present invention relates to a method of analyzing a mixture containing estrogenic compounds. The method comprises the steps of preparing a solution containing estrogenic compounds and analyzing the estrogen containing solution utilizing an HPLC system. The estrogenic compounds to be analyzed preferably include a mixture of conjugated estrogen compounds. More preferably, the mixture is present in Premarin® (conjugated estrogens tablets, USP) or in the composition of matter of the present invention.

The estrogen containing solution includes a mobile phase. The mobile phase may include an organic portion, an aqueous portion, and one or more diluents. Preferably the organic portion and the aqueous portion act as diluents. The estrogen containing solution may be prepared in various ways. The mixture of estrogenic compounds may first be mixed with the organic portion, the aqueous portion, or both followed by mixing the resulting organic portion with the resulting aqueous portion. Alternatively, the organic portion and the aqueous portion may first be mixed together to form a mobile phase followed by mixing the mixture of estrogenic compounds with the mobile phase. The mixture of estrogenic compounds is preferably first mixed with the organic portion followed by mixing the resulting organic portion with the aqueous portion. The mobile phase includes preferably between about 55 and about 90 percent, more preferably between about 65 and about 80 percent, and most preferably between about 70 and about 75 percent aqueous portion. The mobile phase also includes preferably between about 10 and about 45 percent, more preferably between about 20 and about 35 percent, and most preferably between about 25 and about 30 percent organic portion, where percent organic or aqueous portion is measured as a percent volume of the mobile phase. The pH of the mobile phase is preferably between about 2.5 and about 7, more preferably between about 2.5 and about 3.5, and most preferably between about 2.8 and about 3.2.

The organic portion may comprise between about 0 and about 30 percent protic solvent and between about 70 and about 100 percent polar aprotic solvent, where percentages are percent by volume organic diluent. The organic portion preferably comprises between about 5 and about 25 percent protic solvent and between about 75 and about 95 percent polar aprotic solvent, more preferably comprises between about 10 and about 20 percent protic solvent and between about 80 and about 90 percent polar aprotic solvent, and most preferably comprises between about 10 and about 15 percent protic solvent and between about 85 and 90 percent polar aprotic solvent. The protic solvent preferably includes lower alkyl alcohols, and more preferably is methanol. The polar aprotic solvent preferably includes lower alkyl nitriles, and more preferably is acetonitrile.

The organic portion may also include an ion-pairing agent. The ion-pairing agent may preferably have a concentration of between about 0.5 and about 2 millimoles/liter organic portion (mM), more preferably between about 0.5 and about 1.5 mM, and most preferably between about 0.5 and about 1.0 mM. The ion-pairing agent is preferably tert-butyl ammonium hydroxide, although other agents may be employed as will be understood by those skilled in the art. The organic portion may also include various components known by one skilled in the art including, but not limited to, buffer salts, acids, and bases.

The aqueous portion may include an ion-pairing agent. The aqueous portion may preferably have an ion-pairing agent concentration of between about 0.5 and about 2 millimoles/liter aqueous portion (mM). More preferably, the aqueous portion has an ion-pairing agent concentration of between about 0.5 and about 1.5 mM, and most preferably between about 0.5 and about 1.0 mM. The ion-pairing agent is preferably tert-butyl ammonium hydroxide, although other agents may be employed as will be understood by those skilled in the art. The aqueous portion has a pH of preferably between about 2.5 and about 7, more preferably between about 2.5 and 3.5, and most preferably between about 2.8 and about 3.2. The aqueous portion may also include various components known to one skilled in the art including, but not limited to, buffer salts, acids, and bases. Preferable buffer salts are phosphate salts.

The analyzing step may be performed utilizing an HPLC system known to one skilled in the art. The HPLC system may preferably include a reversed phase column. The column has a length and an inside diameter. The length of the column may be between about 5 and about 100 cm. The length of the column is preferably between about 5 and about 30 cm, more preferably between about 10 and about 20 cm, and most preferably 15 cm. The inside diameter of the column may be between about 2 and about 100 mm, and is preferably between about 3 and about 50 mm, more preferably between about 3 and about 20 mm, and most preferably between about 3 and about 10 mm. The column is preferably packed with an alkyl based stationary phase. The alkyl based stationary phase is preferably a $C_{18}$ stationary phase. The particle size of the stationary phase is preferably between about 2 and about 20 $\mu$m, and is more preferably between about 2 and about 10 $\mu$m.

The HPLC system may include one or more suitable detectors. The detectors preferably include fluorescence and ultraviolet (UV) detectors. The UV detector preferably includes a diode array. The UV detector detects at a wavelength preferably between about 190 and about 400 nanometers (nm), more preferably between about 200 and about 300 nm. The fluorescence detector preferably has an excitation between about 250 and about 310 nm, more preferably between about 260 and about 300 nm, and most preferably between about 270 and about 290 nm. The fluorescence detector preferably exhibits emissions between about 300 and about 320 nm and between about 395 and 415 nm, more preferably between about 305 and about 315 nm and between about 400 and about 410 nm.

The HPLC system may have certain operating parameters including column flow rate and column temperature. The column flow rate is preferably between about 0.1 and about 10 milliliters/minute (mL/min), more preferable between about 2 and about 5 mL/min, and most preferably about 3 mL/min. The column temperature may be preferably between about 10 and about 35° C., more preferably between about 15 and about 30° C., and most preferably about 25° C. While the foregoing parameters may be preferred, other parameters may be employed as will be understood by those skilled in the art.

The analyzing step may further comprise the step of collecting the peaks of interest and preferably comprises the step of fraction collecting the peaks of interest. The fraction collecting step is preferably performed using a multi-channel fraction collector.

Methods of the present invention may be performed as a part of a method for characterizing naturally derived equine conjugated estrogens (i.e. Premarin® (conjugated estrogens tablets, USP)) to determine the essential estrogenic compounds thereof. Methods for characterizing Premarin® (conjugated estrogens, USP) will now be described in the following Examples. In the Examples, "mL" means milliliter, "° C." means degrees Celcius, "mM" means millimoles/liter, "M" means moles/liter, "Å" means angstrom, "$\mu$m" means micrometer, "nm" means nanometer, "mm" means millimeter, "mg" means milligram, "m/z" means mass to charge ratio, "(M+H)$^+$" means protonated parent ion (in mass spectrometry), and "(M–H)" means parent ion (in mass spectrometry). These Examples are provided to illustrate the invention and are not intended to limit the invention as set forth by the claims.

Example 1

Characterization of Premarin® (Conjugated Estrogens, USP)

I. Criteria for Characterizing Compounds as Essential Estrogenic Compounds

Two fundamental criteria have been used as the basis for determining essential estrogenic compounds in this analysis. First, the lot-to-lot consistency of any given component reflects the control of that component in the manufacturing process and/or its stability. A conservative approach to eliminating estrogenic compounds from consideration as essential estrogenic compounds by their respective lot-to-lot variability has been taken. Only those components with a variability of ±50% were eliminated.

The second criterion may be the most critical: the assignment of potential active ingredients requires a definition of estrogenicity. A structure-function approach to defining estrogenicity was taken. According to *Goodman & Gilman's The Pharmacological Basis of Therapeutics* (9th Ed., 1996, p. 1412), estrogenic activity is controlled by the presence of the phenolic A ring (at carbon 3) and a β-hydroxyl or ketone group in position 17 of the D ring. The reference states that "the phenolic A ring is the principal structural feature responsible for selective, high-affinity binding to estrogen receptors. Most alkyl substitutions of the phenolic A ring impair such binding, but substitutions on rings C or D may be tolerated." All known estrogens are distinguished by the presence of this phenolic A ring, which confers unique spectroscopic characteristics upon potentially estrogenic compounds. The use of this chemical/spectroscopic approach provides a more conservative method to assign potential estrogenicity than other methods that have been described previously. Biological assays, for example, have yielded conflicting results due to differences in assay systems that reflect differences in tissue-specific responses and in metabolic activation or degradation of specific estrogens., Estrogen receptor binding assays have been proposed as a reasonable measure of relative estrogenicity. However, the existence of at least two receptor subtypes complicates the interpretation of these assays. Finally, animal testing (in rodents, for example) has also been poorly predictive of estrogenicity in humans. Therefore, the chemical/spectroscopic strategy was adopted for this analysis.

II. Summary of Experimental Studies
  A. Instruments and Equipment
    1. HPLC Chromatographic Procedures
      a. HP 1100 HPLC chromatographic system
      b. HP 1100 Diode-array detector
      c. HP1100 Quaternary HPLC pump
      d. Shimadzu, Model RF-551, fluorescence detector
      e. AAI variable speed grinder (U.S. Pat. No. 5,733,173 to Whittle et al.) with 5" grinders and 3" pucks
    2. Fraction Collection, Purification, and Crystallization
      a. ISCO Foxy Jr., 10 Channel Fraction Collector
      b. Büchi, Model R-124 rotary evaporator
      c. SPE cartridge, $C_{18}$, Varian
      d. SPE cartridge, SCX ion-exchange, Varian
    3. Polarized Optical Microscopy
      a. Meiji, Model EMZ-TR, stereomicroscope, with cross polarized lenses
      b. Olympus, Model BH-2, compound microscope, with cross polarized lenses
    4. Mass Spectral Analyses
      a. Electron Impact/Mass Spectrometry (EI-MS)
        1. Instrument: VG Analytical ZAB 2-SE
        2. Source temperature: 200° C.
        3. Electron voltage: 70 eV
        4. Sample probe: Solid Probe
        5. Probe temperature: 280° C.
      b. Liquid Chromatography/Mass Spectrometry (LC-MS)
        1. HP 1100 Binary pump with vacuum degasser
        2. Solvent A: 0.1% aqueous TFA
        3. Solvent B: ACN:water (9:1) v/v containing 0.1% TFA
        4. Gradient: 15% B raised to 40% B in 35 minutes
        5. Flow rate: 0.25 mL/minute
        6. Stationary phase: $C_{18}$ Column
        7. Column temperature: 35° C.
        8. Detector: variable wavelength UV, 220 nm
        9. MS Instrument: VG BioQ triple quadrupole mass spectrometer
        10. Operation mode: positive electrospray ionization (+ESI) mode
        11. Source temperature: 80° C.
      c. Fast Atom Bombardment (FAB-MS)
        1. Instrument: VG Analytical ZAB 2-SE
        2. Sample input: Cesium ion gun
        3. Data system: VG Analytical 11-250J with PDP 11/73
      d. Electrospray Mass Spectrometer (ESI-MS)
        1. Instrument: VG Biotech Bio-Q with quadrupole analyzer
        2. Operation mode: negative ion direct infusion
        3. Injection volume: 30 EL/minute
      e. Electrospray MS/MS (ESI-MS/MS)
        1 Instrument: VG Quattro II Bio-Q triple quadrupole analyzer
        2. Collision gas: argon
        3. Sample aliquot: 50 µL
        4. Elution solvent: 50% aqueous ACN
        5. Flow rate: 10 µL/minute
      f. High Resolution Mass Spectrometer (HR-MS)
        1. Instrument: VG Analytical ZAB 2-SE
        2. Sample input: Cesium ion gun
        3. Data System: VG Analytical 11-250J with PDP 11/73
        4. X-ray Diffraction Single Crystal Analyses
    5. X-ray Diffraction Single Crystal Analyses
      a. Nonius CAD4, Model 586, automated single crystal diffractometer
      b. Cu X-ray tube, fine focus, ($\lambda$=1.5418Å)
      c. Random orientation photographic attachment, Polaroid, Model 57-3
      d. EXPRESS Data collection software
      e. MOLEN Data interpretation software
    6. Scanning Electron Microscopy/Energy Dispersive X-ray Analyses (SEM/EDX)
      a. Hitachi SEM, Model S-3200N
      b. Kevex EDX
  B. Chemicals, Reagents, and Analytical Materials
    1. Chemicals and Reagents
      a. Acetonitrile (ACN), HPLC grade
      b. Methanol (MeOH), HPLC grade
      c. Ethanol, absolute
      d. Milli-Q water
      e. Triethylamine (TEA), HPLC grade
      f. tert-Butyl ammonium hydroxide (TBAH), 0.4 M, reagent grade
      g. Tetramethylphosphonium chloride, reagent grade
      h. Potassium phosphate monobasic, AR grade
      i. Nitrogen gas, zero grade
      j. Phosphoric acid
      k. Hydrochloric acid
    2. Analytical Samples
      a. Various Premarino lots used are detailed in Table 1 below:

TABLE 1

| Lot Number | Product Form | Label Claim (mg) | Country | Exp. Date |
|---|---|---|---|---|
| 2ZAD-F4 | Tablet | 0.625 | Canada | June 1998 |
| 2YPX-F4 | Tablet | 1.25 | Canada | June 1998 |
| B0238 | Tablet | 0.625 | UK | April 1997 |
| B0291 | Tablet | 1.25 | UK | April 1997 |
| 9961463 | Tablet | 0.625 | USA | May 2001 |
| 9961447 | Tablet | 1.25 | USA | April 2001 |
| 9940168 | Tablet | 0.625 | USA | October 1998 |
| 9940242 | Tablet | 1.25 | USA | October 1998 |
| 9930519 | Tablet | 1.25 | USA | August 1995 |
| 7EDN1 | Tablet | 1.25 | USA | June 1992 |
| 7PFC2 | Tablet | 1.25 | USA | August 1989 |
| 3980226 | IV | 25 | USA | January 2003 |
| 3970953 | IV | 25 | USA | July 2002 |
| 3970033 | IV | 25 | USA | February 2001 |

3. Analytical Standards
      a. Conjugated Estrogens Reference Standard (nine component), Organics/LaGrange, Inc. (OLG).
      b. Conjugated Estrogens Reference Standard (ten component), OLG
      c. Estrone, USP
      d. Equilin, USP
      e. 17α-Dihydroequilin, USP
      f. Estrone sulfate, sodium salt, OLG
      h. 17α-Estradiol sulfate, sodium salt, OLG
      i. 17α-Dihydroequilin sulfate, sodium salt, OLG
      j. $\Delta^{8,9}$-Dehydroestrone sulfate, sodium salt with TRIS, OLG 4. Related Standards/Samples
  a. 1,3,5(10),6-Estratetraen-3,17β-diol, Research Plus
  b. 3-Indoxy sulfate, potassium salt (Indican), Sigma
  c. Hippuric acid, ACROS
  d. o-Methylhippuric acid, ACROS
  e. m-Methylhippuric acid, ACROS
  f. p-Methylhippuric acid, ACROS
  g. d,l-Mandelic acid, ACROS
  h. Creatinine, ACROS
  i. Benzoic acid, sodium salt, Chem Service
  j. 4-Picoline, Aldrich
  k. Uric acid, ACROS
  l. D-Glucoronic acid, Aldrich
  m. Biopterin, Aldrich
  n. 4-Pyridoxic acid, Aldrich
  o. Indole, Sigma
  p. Equol, Fluka
  q. 1,3,5(10)-Estratrien-3,17β-diol-3,17 disulfate disodium, Research Plus
  r. 1,3,5(10)-Estratrien-3,17β-diol-17-sulfate sodium, Research Plus
  s. 1,3,5(10)-Estratrien-2,3,17β-triol, Research Plus
  t. 1,3,5(10)=Estratrien-2,3-diol-17-one-2-methyl ether, Research Plus
  u. 1,3,5(10)-Estratrien-2,3,17β-triol-2-methyl ether, Research Plus
  v. 1,3,5(10)-Estratrien-3-ol-17-one-3-methyl ether, Research Plus
  w. 1,3,5(10)-Estratrien-3,17β-diol-3-methyl ether, Research Plus
  x. 1,3,5(10)-Estratrien-2,3,17β-triol-2,3-dimethyl ether, Research Plus
  y. 1,3,5(10)-Estratrien-3,16α,17α-triol, Research Plus
  z. 1,3,5(10)-Estratrien-3,16 α,17β-triol, Research Plus
  aa. 1,3,5(10)-Estratrien-3,16α,17β-triol-3-sulfate sodium, Research Plus
  bb. 1,3,5(10)-Estratrien-3,16α,17β-triol-16,17 disulfate disodium, Research Plus
  cc. 1,3,5(10),6-Estratetraen-3-ol-17-one, Research Plus
  dd. 5α-Androstan-3β,16α-diol, Research Plus
  ee. 5α-Androstan-3β,16β-diol, Research Plus
  ff. 5α-Androstan-3β,17α-diol, Research Plus
  gg. 5α-Androstan-3β-ol-16-one, Research Plus
  hh. 5α-Androstan-3α-ol-17-one-3 sulfate sodium, Research Plus
  ii. 5α-Pregnan-3β,20α-diol, Research Plus
  jj. 5α-Pregnan-3β,20β-diol, Research Plus
  kk. 5α-Pregnan-3β-ol-20-one, Research Plus
  ll. 4-Pregnen-20β-ol-3-one, Research Plus
  mm. 16,5α-Pregnen-3β-ol-20-one, Research Plus
C. Methods
1. HPLC Chromatographic Assay Method A standard solution containing about 0.03 mg/mL of Conjugated Estrogens Drug Substance may be prepared as follows. Weigh an appropriate amount to yield 200 mL of solution. Dissolve this amount in 61 mL of organic diluent and mechanically shake for 10 minutes. Add about 100 mL of aqueous diluent and mechanically shake for 10 minutes. Dilute to volume with aqueous diluent and mix well. Filter a portion of the solution through a 0.45 μm PTFE filter.

A free stock steroid solution of estrone, equilin and 17α-dihydroequilin in methanol at 0.2 mg/mL may be prepared for each free estrogen.

A resolution solution containing about 0.03 mg/mL of ten-component conjugated estrogens reference standard and approximately 0.006 mg/mL each of 17α-dihydroequilin, equilin and estrone as for the standard solution may be prepared. Preferably, a volume of 100 mL of resolution solution is prepared, mixed and filtered as for the standard solution.

A phosphate buffer solution may be prepared. The phosphate buffer solution is preferably a 50 mM potassium phosphate buffer solution.

An aqueous diluent containing a solution of phosphate buffer and 0.4 M TBAH with a volumetric ratio of 277:0.9 may be prepared. The pH of the solution may be adjusted to 3.0±0.1 with phosphoric acid.

An organic diluent containing a solution of acetonitrile and methanol with a volumetric ratio of 26.5:4 may be prepared.

A mobile phase may be prepared by mixing a solution of organic diluent and aqueous diluent with a volumetric ratio of 30.5:69.5.

Samples to be analyzed may be prepared. First, tablets are prepared by washing 10–20 tablets in water to remove the outer coating then blowing them to dryness under a nitrogen purge. The tablets are then ground to a fine powder using either a mortar and pestle or the AAI grinder at 450 RPM for 1 minute. The ground tablets are then mixed with the mobile phase to form a mobile phase containing conjugated estrogens.

For example, when 0.625 mg tablets are to be analyzed, the equivalent weight of ten tablets is placed into a 200 mL volumetric flask. Next 61 mL of organic diluent are added to the flask and the flask is mechanically shaken for ten minutes. Then, about 100 mL of aqueous diluent is added to the flask and the flask is mechanically shaken for ten minutes. The resulting solution is then diluted to volume with aqueous diluent and mixed. A portion of the solution is filtered through a 0.45 μm PTFE filter.

As another example, when 1.25 mg tablets are to be analyzed, the equivalent weight of ten tablets is placed into a 400 mL volumetric flask. Next 122 mL of organic diluent is added to the flask and the flask is mechanically shaken for ten minutes. Then, about 200 mL of aqueous diluent is added to the flask and the flask is once again mechanically shaken for ten minutes. The resulting solution is then diluted to volume with aqueous diluent and mixed. A portion of the solution is filtered through a 0.45 μm PTFE filter.

When 25 mg Intravenous Lyophilized Cake is to be analyzed, the vial is opened, and about 5 mL of mobile phase is added to the vial. The vial is then shaken briefly until the cake has visibly dissolved. The solution is quantitatively transferred to a 200 mL volumetric flask, diluted to volume with mobile phase, and mixed. 5.0 mL of this solution are pipetted to a 10 mL volumetric flask, diluted to volume with mobile phase, and mixed well.

In this chromatographic analysis, an HPLC system with a column heater equipped with a 3 μm, 15.0 cm×4.6 mm $C_{18}$ column and suitable UV detector for detection at 220 nm and diode array was employed. The flow rate was set for 1.5 mL/minute and the column temperature was set for 25° C.

An example of a chromatographic procedure is as follows: 100 μL of resolution solution and a diluent blank were separately injected into the chromatograph. No interferences were observed at the relative retention times (RRTs) for any of the known estrogen peaks in the blank injection. Equal volumes of the standard solution and the sample preparations were separately injected into the chromatographic systems. Each peak was integrated and evaluated based on the peak area responses for the ten known estrogen peaks.

The procedures described above were used to obtain the chromatogram of Premarin® (conjugated estrogens tablets, USP) illustrated in prior art FIG. 1. Similar procedures were used to obtain the chromatogram of the present invention illustrated in FIG. 2. In FIGS. 1 and 2, the labeled peaks are as follows: 17β-dihydroequilenin (10, 20); 17β-dihydroequilin sulfate (11, 21); 17α-dihydroequilenin (12, 22); 17β-estradiol sulfate (13, 23); 17α-dihydroequilin (14, 24); 17α-estradiol sulfate (15, 25); equilenin sulfate (16, 26); $\Delta^{8,9}$-dehydroestrone sulfate and equilin sulfate (17, 27); and estrone sulfate (18, 28).

2. Semi-preparative HPLC System for Fraction Collection of Conjugated Estrogen Constituents An enhanced gradient separation allowed a fraction collector to be added to an HPLC system to separate and retain individual peaks or sections of the chromatographic run described above. A Semi-Preparative HPLC Method employed a mobile phase A and a mobile phase B. Mobile phase A was an aqueous phase that included 0.9 mM TBAH and 0.075% 12.1 N HCl, with all percentages by volume mobile phase A. Mobile phase B was an organic phase that included 0.9 mM TBAH, 13.1% MeOH, 86.9% ACN and 0.075% 12.1 N HCl, with all percentages by volume mobile phase B.

Samples to be analyzed may be prepared. First, about 100–200 tablets are washed in water to remove the outer coating then blown to dryness under a nitrogen purge. The tablets are then ground in the AAI grinder at 450 RPM for 1 minute. A solution having a concentration of 0.31 mg/mL conjugated estrogens may be prepared as for the analytical standard solution described above. For example, the equivalent weight of 100 1.25 mg tablets are placed in a 400 mL volumetric flask. 122 mL of organic diluent is added to the flask and the flask is mechanically shaken for ten minutes. About 200 mL of aqueous diluent is then added to the flask and the flask is again mechanically shaken for ten minutes. The resulting solution is then diluted to volume with aqueous diluent and mixed. A portion of the solution is filtered through a 0.45 μm PTFE filter.

In this semi-preparative chromatographic analysis, an HP 1100 HPLC system with a column heater equipped with a 7 μm, 15.0 cm×7.8 mm $C_{18}$ column and suitable UV detector for detection at 220 nm and diode array was used. The flow rate was set for 3.0 mL/min and the column temperature was set for 25° C. The gradient profile is listed below:

| Time (min) | % A | % B |
| --- | --- | --- |
| 0.0 | 79.5 | 20.5 |
| 4.0 | 79.5 | 20.5 |
| 16.0 | 63.5 | 36.5 |
| 16.1 | 40.0 | 60.0 |
| 18.0 | 40.0 | 60.0 |
| 18.1 | 79.5 | 20.5 |

An example of a chromatographic procedure is as follows: 1.0–1.5 mL of the sample was injected multiple times on the chromatographic system and the peaks of interest were fraction collected using a multi-channel fraction collector. Cross over of the peak identity to the analytical procedure was performed using diode array comparison to follow peak movement. Once all of the fractions were collected, each fraction was passed through an appropriate ion-exchange column to remove the ion-pairing reagent. The fractions were concentrated using a rotary evaporator under vacuum to an appropriate volume and set aside to allow crystal growth or perform analyses by other means for identification.

III. Characterization of the Essential Estrogenic Compounds in Premarin® (conjugated estrogens, USP)

Premarin® Lot Selection

To adequately characterize Premarin, a variety of lots were examined to investigate the variability of the product. Individual lots of Premarin® tablets were randomly selected which allowed evaluation of consistency between lots and country of origin as well as stability based on aged samples. Table 1 described above details the selection of lots to examine these parameters. Based on product monographs for the Premarin® line, two other products are manufactured using Conjugated Estrogens, USP in addition to Premarin® tablets. These are Premarin® vaginal cream and Premarin® intravenous (IV). Premarin® intravenous lots were also examined to ensure that peaks observed from Premarin® tablets come from Conjugated Estrogens, USP. Premarin® intravenous lots examined are included in Table 1, described above.

The selected tablet lots allowed direct comparison of Premarin® lots from various countries of origin, the most popular tablet strengths, and aged samples of 1.25 mg tablets covering lots with expiration dates at three-year intervals. From these samples the characterization of the components of Premarin® was carried out by closely examining each individual peak by the HPLC Chromatographic Assay Method described above. Components which were present at consistent levels greater than 0.1% in the lots examined were considered for investigation as potential essential estrogenic compounds. Consistency was one of the elements considered when determining if a compound was a potential essential estrogenic compound, and was defined as a variation of the amount found in the current Premarin® lots of less than ±50%.

Characterization—HPLC Strategy and Scheme

This characterization began by using an HPLC chromatographic method validated for quantitation of the nine-component Endeavor synthetic conjugated estrogens drug product (available from Endeavor Pharmaceuticals of Wilmington, N.C.). The method was modified slightly to optimize resolution of Premarin® components. This method is the HPLC Chromatographic Assay Method described above. All individual peaks discussed in this report are identified by relative retention time (RRT), based on estrone sulfate as the reference peak.

Samples from the various tablet lots were analyzed by HPLC and overlaid to compare differences. On a first examination of the overlay, all of the chromatograms were visually similar. The similarities among the various lots allowed selection of a single lot (Lot 7 PFC2) to visualize the characterization.

Based upon published information about the formulation of Premarin® tablets, 15 different excipients, six different dye components, and a mobile phase blank were injected and compared by retention time and diode array analysis to the chromatograms obtained from intact tablets. From these chromatograms, one peak was found which corresponded to a peak found in Premarin®. The mobile phase blank exhibited a peak at an RRT of 0.069, which matched the same peak in shape and size in Premarin®. Overlays of the diode array spectra of the mobile phase peak and the peak found in Premarin® confirmed the peaks to be the same.

Identification of the ten USP-listed sodium estrogen sulfate components (listed below in Table 2) was performed by injection of appropriate analytical standards on the chromatographic system. Peaks obtained were matched to the Premarin® chromatograms by comparison of relative retention times and diode array spectra.

TABLE 2

Conjugated Estrogens, USP sodium estrone sulfate
sodium equilin sulfate
sodium 17α-dihydroequilin sulfate
sodium 17β-dihydroequilin sulfate
sodium 17α-estradiol sulfate
sodium 17β-estradiol sulfate
sodium equilenin sulfate
sodium 17α-dihydroequilenin sulfate
sodium 17β-dihydroequilenin sulfate
sodium $\Delta^{8,9}$-dihydroestrone sulfate From the chromatograms of the tablet lots tested, approximately 76 peaks are seen by UV detection at 220 nm. Of these peaks, one has been shown to be from the mobile phase blank, and nine peaks are from the ten known components. Full baseline resolution was not achieved with this method for sodium equilin sulfate and sodium $\Delta^{8,9}$-dehydroestrone sulfate. These compounds are structural isomers varying only in the double bond position in the B ring. At the concentration injected on the column for this analysis, these peaks coalesce. These peaks were resolved using the HPLC Assay Method described below in Example 2. There are 32 other peaks present at <0.1% peak area relative to the total peak area of the ten known sodium estrogen sulfate components.

Related Compound Considerations

Each sulfated ketone can have a corresponding sulfated 17α- and 17β-hydroxy derivative; each of these can then hydrolyze to form the non-sulfated species. This results in a total of six possible analogs for each basic ketone ring structure. There are four known basic ring structures represented by the sulfated ketones: estrone, equilin, equilenin, and $\Delta^{8,9}$-dehydroestrone. Therefore, this generates the possibility of up to 24 related compounds.

During a previous analytical HPLC method validation study, authentic USP standards of three non-sulfated related substances (17α-dihydroequilin, equilin, and estrone) were injected to prove their retention characteristics. Three more non-sulfated species (β-estradiol, equilenin, and 17β-dihydroequilenin) were found to be present in the 1,3,5(10), 6-estratetraen-3,17β-diol standard and identified by their elution order and spectral properties. The ratios of the RRT values of the ten known sulfated and six non-sulfated species of the ketone and diol forms were examined to evaluate patterns. Table 3 shows the known ratios of the relationships of the RRT values of the various sulfated and non-sulfated species.

TABLE 3

| Sample | RRT Values | | Ratio |
|---|---|---|---|
| Sulfate to Non-Sulfated Hydrolysis | Sulfated | Non-Sulfated | |
| Estrone | 1.000 | 1.750 | .175 |
| 17β-Estradiol | 0.574 | 1.096 | 1.91 |
| Equilin | 0.896 | 1.554 | 1.73 |
| 17α-Dihydroequilin | 0.666 | 1.162 | 1.74 |
| Equilenin | 0.816 | 1.398 | 1.71 |
| 17β-Dihydroequilenin | 0.417 | 0.710 | 1.7 |
| Keto-to α-Diol Correlation | Ketone | α-Diol | |
| Estrone sulfate | 1.000 | 0.792 | 1.26 |
| Equilin sulfate | 0.896 | 0.666 | 1.35 |
| Equilin | 1.554 | 1.162 | 1.34 |
| Equilenin sulfate | 0.816 | 0.556 | 1.47 |
| Keto-to β-Diol Correlation | Ketone | β-Diol | |
| Estrone sulfate | 1.000 | 0.574 | 1.74 |
| Estrone | 1.750 | 1.096 | 1.60 |
| Equilin sulfate | 0.896 | 0.482 | 1.86 |
| Equilenin sulfate | 0.816 | 0.417 | 1.96 |
| Equilenin | 1.398 | 0.710 | 1.97 |
| α-Diol to β-Diol Correlation | α-Diol | β-diol | |
| Estradiol sulfate | 0.792 | 0.574 | 1.38 |
| Dihydroequilin sulfate | 0.666 | 0.482 | 1.38 |
| Dihydroequilenin sulfate | 0.556 | 0.417 | 1.33 |

Based upon the ratios of the RRT values, a logical correlation was developed and used to predict the position of peaks based upon RRT. From this predicted RRT for the unknown peaks, diode array and fluorescence spectra were used to examine the peaks near the predicted RRT for comparison to the spectral characteristics of known related compounds.

Fluorescence and UV Absorption Spectral Considerations

Volume 12 of *Analytical Profiles of Drug Substances* (K. Florey, ed., Academic Press, NY, 1983, pp. 231–257) details the fluorescent behavior of estrone. Estrone, when excited at 280 nm, shows a sharp fluorescence peak at 307 nm due to the phenolic chromophore emission, and a second, broad peak at about 410 nm. Since estrogenic activity and binding to estrogen receptors requires the presence of a phenolic A ring (Goodman and Gilman, 1996, p. 1412), a spectroscopic examination of the various peaks can identify components with structural characteristics associated with the potential for estrogenicity. The fluorescence detector was introduced in series into the chromatographic system and the excitation and emission wavelengths were optimized to enhance the signals of the chromatographic peaks at 312 nm and 405 run in Premarin®. Overlays of the two fluorescence chromatograms with the UV chromatogram were used to examine the peaks for spectral characteristics of potential estrogenic components. The ten USP-defined sodium estrogen sulfates all exhibit fluorescent emissions at 312 run and most also show the emission at 405 nm. From these spectral overlays, 11 additional peaks were observed which exhibited a fluorescence emission at one or both of the emission wavelengths at a specific retention time where UV absorption was not detectable. This lack of detectable UV absorption was due either to the overlap with a larger peak or the lack of UV absorption above ~0.01%. Since there was no quantifiable UV peak, these 11 peaks were considered as<0.1% peak area and the RRT values were estimated based upon the RRT value of the surrounding peaks. This brings the total number of peaks to 87 and the number of insignificant peaks eliminated as<0.1% to 43.

Fluorescence spectral information also can be used in the characterization of Premarin® for screening the chromatographic peaks and eliminating them as non-estrogenic. If peaks did not exhibit fluorescence at one of the two wavelengths, they were considered non-estrogenic due to the lack of the required phenolic A ring responsible for specific estrogen receptor binding. There were a total of 22 peaks that did not fluoresce. Eight of these peaks were >0.1%, and one of these has been identified as the mobile phase peak. Therefore, seven non-estrogenic peaks>0.1% (RRT values of 0.102, 0.121, 0.198, 0.441, 0.647, 0.705, and 1.045) present in Premarin® were identified as non-estrogenic by this criterion.

All known naturally occurring estrogens have in common a phenolic functional group at position 3 of the A ring with varying degrees of saturation in the adjoining fused B ring system. The UV spectral characteristics are controlled by this phenolic chromophore and shifts may occur dependent upon the degree of conjugation. The basic phenolic chromophore exhibits auxochromic UV maxima for the aromatic $\pi \rightarrow \pi^*$ $E_2$ band at about 210 nm and a maxima for the $\pi \rightarrow \pi^*$ B band at about 270 nm. These maxima can shift in both wavelength and intensity dependent upon the degree of saturation of the attached groups. The absence of these UV bands for a given peak is indicative of the absence of the phenolic chemical moiety and thus the absence of the estrogenic potential of the component.

When the diode array spectra of peaks greater than 0.1% were examined, a total of eight peaks were found (RRT values of 0.074, 0.102, 0.170, 0.321, 0.376, 0.441, 0.450, and 0.705) which did not exhibit a diode array spectra characteristic of an estrogen. Of these eight, three were found (RRT values of 0.102, 0.441, and 0.705) to also be non-estrogenic based upon fluorescence spectra.

The ten USP-defined conjugated estrogens consist of the sulfated forms of estrone, equilin, and equilenin present in both the ketone and the 17α and 17β-hydroxy forms to give the first nine components and $\Delta^{8,9}$-dehydroestrone sulfate as the tenth. Overlays of the diode array spectra of the three sulfated forms of estrone, equilin, and equilenin were prepared. Each set of diode array spectra all exhibited similar spectral characteristics. Based upon this, and the predicted RRT values for the two sulfated diols of $\Delta^{8,9}$-dehydroestrone sulfate, the predicted peaks (RRT values of 0.466 and 0.625) were examined by both diode array and fluorescence spectra and were found to correspond to the sulfated diols as expected. This brings the number of sulfated estrogens present in Premarin® to 12.

Each of these 12 sulfated compounds can also undergo metabolism or degradation by hydrolysis to desulfonate the compound. Samples of non-sulfated estrone, equilin, 17α-dihydroequilin, 17β-estradiol, 17β-dihydroequilenin, and equilenin were available to examine Premarin® for the presence of non-sulfated forms. The diode array spectra of each of these six samples were compared to the corresponding sulfated ketone spectra. Examination of the overlays revealed that in the estrone and equilin based systems, where only one aromatic ring was present (Ring A), there was a corresponding bathochromic (red) shift of the UV spectral maxima to longer wavelengths by about 5 nm. This shift may be due to shifts in the electron density of the aromatic $\pi \rightarrow \pi^*$ transition from the loss of the sulfate. In the equilenin based systems, where two fused aromatic rings are present (Rings A and B), a hypsochromic (blue) shift of the UV spectral maxima to shorter wavelengths by about 2 nm was observed. This shift may be due to the more extended conjugated aromatic system present as well as the loss of the sulfate group.

Based upon the chemical structure of $\Delta^{8,9}$-dehydroestrone, and the RRT predictions, Premarin® was examined for the non-sulfated $\Delta^{8,9}$-dehydroestrone peak. The position of the double bond at the 8,9 position may allow more extended conjugation than is present in estrone and equilin, but less than in equilenin, so the UV shift was predicted to be somewhere in between, with little or no shift observed. The predicted region was examined for the non-sulfated $\Delta^{8,9}$-dehydroestrone, and the peak was found at an RRT value of 1.589, which matched the expected diode array spectrum with essentially no UV shift.

Elucidation of Premarin® Peaks

The remaining five non-sulfated peaks were predicted to occur in regions where there was little or no UV absorption or where another large peak was present. This hindered the comparison of the diode array spectra, but at each of the predicted RRT values, the fluorescence spectra showed emissions which were consistent with the assignments, and the level of each of the non-sulfated component was <0.1%. These mathematical pattern predictions and spectral analyses accounted for all 24 derivatives of the four known sulfated ketones.

Ten of the 24 identified peaks found were $\leq 0.1\%$. This leaves 33 other insignificant peaks which can be eliminated since they are $\leq 0.1\%$.

At this point, this process has accounted for 56 of the 87 peaks detected in Premarin®. Examination of the peaks showed that thirteen of the peaks are $\leq 0.5\%$, seven are >0.5 and $\leq 1.0\%$, five are >1.0 and $\leq 2.0\%$, and only six are >2.0%. Using the fluorescent and diode array spectroscopic data on these 31 peaks, 12 peaks are observed that did not demonstrate spectra characteristic of an estrogenic compound. However, the peak at RRT of 0.198, which was observed at up to 10%, was investigated further in spite of the lack of evidence for estrogenicity, since it was present at a relatively high level.

Remaining Peaks for Investigation

Twenty unknown peaks, including the peak at RRT of 0.198, were selected for careful examination and characterization. Of these, seven of the peaks are <0.5%, four of them are >0.5 and $\leq 1.0\%$, four are >1.0 and $\leq 2.0\%$, and only five are >2.0%.

The 20 remaining peaks demonstrated that most of the significant unknown peaks occur in the first seven to eight minutes (up to RRT of about 0.450) of the chromatogram. Beyond this RRT, only four unknown peaks occur: one at an RRT of 0.515 (1.3–1.5%); a second at an RRT of 0.601 (~1.0%); a third at an RRT of 0.738 (0.2–0.3%); and a fourth at an RRT of 0.971 (1.4–1.7%). Highlighting just the 20 unknown peaks of interest in the chromatogram shows that the five major peaks are found in the first four minutes. These five peaks dominate the total percent peak area of the unknown peaks and account for over 90% of the total unknown peak area, and are roughly equal to the total peak area of the ten active estrogenic components listed in Conjugated Estrogens, USP.

With the focus clearly directed toward the 20 unknown peaks, and primarily upon the five major peaks that comprise 90% of the unknown peak area, methodology and techniques were developed for the resolution, isolation, and purification of each of these peaks. Due to the overlap of peaks in the first four minutes of the run, a new gradient HPLC method utilizing a semi-preparative column was developed to increase the column load and resolution of the major peaks. With this Semi-Preparative HPLC Method described above, the sample load on the column was increased 50–75 times the analytical level and the individual peaks of interest were all fully resolved from the other major peaks. The larger peak identities in the first four minutes of the chromatogram were monitored by slow changes to the gradient and were confirmed by diode array analysis. The five major peaks of interest are identified as peaks 1, 4, 6, 7, and 8 and corresponded to the previous RRT values of 0.056, 0.092, 0.142, 0.185, and 0.198, respectively. Using the new gradient method, the elution order and the RRT values of the peaks have changed significantly, so these five peaks will be referred to using their assigned identification number rather than their RRT value.

Using the original HPLC method, a study was conducted in which the ion-pairing agent concentration of the mobile phase was varied to investigate the shifts in retention time and changes in elution order of the peaks. This study of the peaks and their behavior under varying mobile phase conditions gave some tentative information about the peak identities. Peaks that shifted to significantly longer retention times with increasing ion-pairing concentration, like peaks 6, 7, and 9, may be expected to be sulfated species. While peaks that showed little or no change in retention time, like peaks 1, 2, 3, 4, 5, and 8, may be expected to be non-sulfated.

Separation and Isolation of the Major Unknown Peaks

The enhanced gradient separation allowed a fraction collector to be added to the system to separate and retain individual peaks or sections of the chromatographic run. The individual peaks of the five major unknowns (peaks 1, 4, 6, 7, and 8), as well as the minor peaks 2, 5, and 9, were isolated from Premarin® by fraction collection using the Semi-Preparative HPLC Method described above. Peak 3 was poorly resolved from peak 4, and peak 9 was only fraction collected in later runs. The fractions were passed through an SCX ion exchange Sep-Pak to remove the ion-pairing agent, further purifying each of the peak fractions. The resulting solutions were neutralized with ammonium hydroxide and were then taken to dryness by the rotary evaporator. The large amount of material left in the recovery flask was mainly composed of the mobile phase buffer and the desired compound. From this solid mixture the compound was extracted and further purified to allow for investigation and possible identification by single crystal X-ray analysis, SEM/EDX, mass spectrometry, and other means. As each of these extracted materials was again brought to dryness by the rotary evaporator, the resultant material tended to be yellowish viscous oils, rather than dry solid materials. Based upon later experiments utilizing LC-MS, it was determined that the yellowish viscous oil was caused by the presence of polyethylene glycol and other excipients in the Premarin® formulation which leached out during the HPLC analysis, raising the baseline of the chromatogram and contaminating each of the fractions. This viscous material hindered crystallization and ultimate purification of the fractions.

Characterization of the Unknown Peaks

Due to the differing chemical nature of each fraction, the investigative methods were varied. Peaks 6 and 7 were thought to be sulfated and will be discussed first. Peaks 4 and 8 appeared to be non-sulfated carboxylic acids and were investigated next followed by peak 1 that appeared non-sulfated also. Over the course of the investigations, multiple fraction collections and purifications were performed. The following individual synopses for each peak represent multiple individual runs and experiments.

Peak 6 Investigation

The original peak 6 fraction from the fraction collector was light blue in color, unlike all the other fractions that were colorless to pale yellow. Peak 6 was extracted from the dry rotary evaporator mixture of buffer and compound using ethanol. This solution was then concentrated on the rotary evaporator to produce a dark yellow viscous oil. When this yellow oil was removed from the rotary evaporator vacuum, it began to rapidly change colors. It changed from yellow to red, to violet, to blue in a matter of minutes, and after several days to weeks changed to brown in color. HPLC chromatography of the colored fraction confirmed that peak 6 in the chromatograms remained unchanged. The color change appeared to be an air oxidation of some minor component present with peak 6. When the yellow oil was isolated and stored under dry nitrogen gas, little or no color change was observed. A portion of this fraction was set aside to attempt crystallization and a portion was sent for LC-MS analysis.

Crystallization attempts utilizing a wide variety of techniques were not highly successful in producing any crystals of peak 6 for single crystal analysis. Clear crystals grew from the blue solution using slow evaporation but were not well formed and were found twinned. These crystals appeared to have a Tetragonal I lattice and a volume of only 390.4Å$^3$. This volume size is too small for an estrogen/steroid and suggests these are simple salts. A better crystal was selected which did not appear twinned and the X-ray analysis was restarted. The unit cell found again was a Tetragonal I lattice with cell constants a=7.459(4)Å, c=7.013(4)Å, and a volume of 390.2(3)Å$^3$. These parameters suggested a simple salt. The data set was collected and space group #122 (14bar2d) was selected based upon the systematic absences. With Z=4, the structure was refined to R factors of 8.9 and 12.4% where the identity of the material was determined to be the mineral archerite ($KH_2PO_4$). A comparison to the ICDD (International Center for Diffraction Data) database shows archerite (Card #35-0807) matches the unit cell and space group found in our analysis. This compound was the buffer used in our HPLC mobile phase and was not considered a part of Premarin® tablets.

Chromatographic UV analysis during LC-MS analysis showed one large peak and three minor peaks in this fraction. The major peak was run under negative ion FAB-MS and showed a single, weak, sample related molecular ion $(M-H)^-$ at m/z 212. Positive ion FAB showed no significant sample related peaks. Negative ion ESI-MS showed an intense molecular ion $(M-H)^{31}$ at m/z 212 consistent with the FAB-MS data. The negative ion ESI-MS/MS spectrum also confirmed the parent ion at 212 m/z. This spectrum showed a number of daughter ions including the ion at 80 m/z consistent with an $SO_3^-$ fragment and an ion at 1·32 m/z consistent with the non-sulfated molecular ion. These results are all consistent with a molecular mass of 213Da and the presence of a sulfate moiety.

The mass spectral data suggest the structure for peak 6 is that of Indican (Metabolic Indican) which, according to *The Merck Index*, occurs in the urine of mammals. An authentic standard of the potassium salt of Indican was purchased from Sigma and was dissolved in mobile phase and injected onto our gradient HPLC system. Overlays of the chromatograms and the diode array spectra of the standard and an injection of Premarin® showed matching retention times and identical diode array spectra for the peaks confirming the identity of peak 6 as indican.

Peak 7 Investigation

Peak 7 was extracted from the dry rotary evaporator mixture of buffer and compound using ethanol. This solution was then concentrated on the rotary evaporator to produce a yellow viscous oil. Portions of this fraction were set aside to attempt crystallization and for submission for LC-MS analysis.

Crystallization attempts utilizing a wide variety of techniques produced several crystals from peak 7 for examination by single crystal analysis. The first of these were large clear crystals grown from the yellow solution using slow evaporation. A piece from one of the large crystals was cleaved and mounted in a 0.4 mm glass capillary for X-ray analysis. The crystal diffracted very strongly and gave a Triclinic lattice with cell constants a=10.063(2)Å, b=10.194(1)Å, c=12.080(2)Å, α=78.79(1)°, β=88.57(1)°, γ=77.21(1)°, and V=1185.1(4)Å$^3$. Although not intending to be bound by theory, based upon a Z=2, such a volume size suggests about 32 non-hydrogen atoms are present in the asymmetric unit. The data set was collected and appeared acentric based upon a Phillip's zero moment test of the data. Structure solution was attempted using space group #1 (P1). The structure was solved and refined to R factors of 5.9 and 7.2 percent where the identity of the material was determined to be a di-phosphate salt of tert-butylamine. At this point completion of the structural analysis was halted since this compound was believed to have formed from the interaction of the mobile phase ion-pairing agent and phosphate buffer, and thus was deemed unimportant. Prior to data solution, SEM/EDX analysis was performed using a piece of this crystal and showed only phosphorus atoms above the normal organic components (C, N, and O) in the crystal.

Yellow cube shaped crystals were also grown from the yellow solution containing peak 7. One of these of about 0.12×0.12×0.12 mm was selected and mounted on the end of a glass fiber. In this instance, the crystal diffracted well and generated a Cubic F lattice of a=12.853(3)Å and a volume of 2123.3Å$^3$. For an F-centered cubic, it is believed that this is not a large enough volume to be more than a simple salt. A search of the ICDD database revealed 2 isomorphic structures with this unit cell. Both were space group #225 (Fm3barm) and were of the general formula [N(CH$_3$)$_4$]$_2$MCl$_6$, where M=Sn(IV), or Zr(IV). A SEM/EDX analysis showed chlorine as expected, but revealed copper or zinc present as the metal ion. This was determined to be an organometallic salt and would not be considered an estrogenic component of Premarin®.

The viscous yellow oil was dissolved in meta-nitro benzyl alcohol matrix and run under positive ion FAB-MS, which generated a major molecular ion (M+H)$^+$ at a m/z of 242. The intensity of this peak was sufficient to permit an HR-MS analysis to generate a molecular composition and an EI-MS to study the fragmentation pattern. HR-MS was used and generated an accurate molecular weight of 242.2841. Based upon that mass, the molecular composition was determined to be C$_{16}$H$_{36}$N. A strong EI-MS spectrum was only achieved at relatively high probe temperatures near 280° C. and showed strong signals at m/z 100, 142, and 185. A library match was performed and showed this to be tert-butylamine, which is consistent with the HR-MS results. This was used as the ion-pairing agent in the mobile phase during fraction collection.

Chromatographic UV analysis during LC-MS analysis shows one large peak and one minor peak in this fraction. The major peak was run under negative ion FAB-MS and showed a single, sample related (M–H)$^-$ molecular ion at m/z 187. Positive ion FAB showed no significant sample related peaks. Negative ion ESI-MS showed a major molecular ion (M–H)$^-$ at mn/z 187 consistent with the FAB-MS data. The negative ion ESI-MS/MS spectrum also confirmed the parent ion at 187 m/z. This spectrum showed a number of major daughter ions including the ion at 80 Mn/z consistent with an SO$_3^-$ fragment and an ion at 107 m/z consistent with the non-sulfated molecular ion. The ion at m/z 92 is consistent with a fragment of toluene. These results are all consistent with a molecular mass of 188Da and the presence of a sulfate moiety. A fraction of this peak was collected from the LC-MS and confirmed by HPLC. The fraction was run on the gradient HPLC system and was shown to be pure, matching the retention time of peak 7 in the Premarin® chromatogram. Overlays of the diode arrays of the two peaks appeared identical confirming the identity of peak 7.

The mass spectral data indicate the molecular formula for peak 7 is C$_7$H$_8$SO$_4$. This peak contains a sulfate and an aromatic ring, which generates a structure of either a sulfated benzyl alcohol or cresol. Authentic standards of these compounds were not commercially available, so direct injection in the HPLC system as confirmation was not possible. The most likely chemical structure for peak 7 is sulfated benzyl alcohol.

Peak 4 Investigation

Peak 4 was extracted from the dry rotary evaporator mixture of buffer and compound using ethanol. This solution was concentrated on the rotary evaporator to produce a yellow viscous oil. Portions of this fraction were set aside to attempt crystallization and for use in other physical testing to characterize the material.

Crystallization was attempted utilizing a wide variety of techniques including slow evaporation. A yellow needle-like crystal with dimensions of 0.08×0.20×0.50 mm was isolated and mounted in a 0.2 mm glass capillary for X-ray analysis. Close inspection of the crystals revealed that the yellow color was due to a thin film coating of the oil and the crystals appeared colorless. Because the yellow film was not crystalline itself, and removal of the film may have damaged the crystals, the crystals were analyzed with the film intact. The crystal diffracted well and gave an Orthorhombic P lattice with cell constants a=8.8921 (9)Å, b=9.1165(4)Å, c=10.5748(7)Å, and a volume of 857.2(2)Å$^3$. This is again a very small volume and for a centric and acentric cell would only give structures of about 6 and 12 non-hydrogen atoms, respectively. The data set was collected and based upon the systematic absences, the acentric space group #19 (P2$_1$2$_1$2$_1$) was selected. Although not intending to be bound by theory, with Z=4 the structure was defined to R factors of 3.5 and 4.3%. The identity of the crystal was determined to be hippuric acid (C$_9$H$_9$NO$_3$) which, according to *The Merck Index*, is found in the urine of herbivorous animals. A search of the ICDD revealed the structure of hippuric acid (Card #30-1748) with this space group and unit cell. An authentic standard of hippuric acid was obtained from ACROS and was dissolved in mobile phase and injected into the gradient HPLC system, described in the semi-preparative method above. Overlays of the chromatograms and the diode array spectra of the standard and an injection of Premarin® showed matching retention times and identical diode array spectra for the peaks confirming the identity of peak 4 as hippuric acid.

Peak 8 Investigation

Peak 8 was extracted from the dry rotary evaporator mixture of buffer and compound using ethanol. This solution was then concentrated on the rotary evaporator to produce a yellow viscous oil. Portions of this fraction were set aside to attempt crystallization and for submission for LC-MS analysis.

Crystallization attempts utilizing a wide variety of techniques produced several crystals from peak 8 for examination by single crystal analysis. The first of these were blue-green prisms. A crystal was chosen and mounted on a glass fiber for X-ray analysis. The crystal diffracted well and gave a Tetragonal P lattice with cell constants a=7.5960(7)Å, c=7.9698(10)Å, and a volume of 459.9(1)Å$^3$. Based upon a Z=8, this volume size suggests about 3 or 4 non-hydrogen atoms in the asymmetric unit. Thus, it is believed that this molecule is most likely a simple salt or possesses internal symmetry. A search of the ICDD database shows that this unit cell corresponds to the structure of (NH4)$_2$CuCl$_4$·2H$_2$O (Card #25-0003) which was in space group #136 (P4$_2$/mnm) with a Z=2 and a unit cell of a=7.59Å and c=7.97Å.

According to *The Merck Index*, ammonium copper(II) chloride is formed from the evaporation of a solution of ammonium chloride and copper(II) chloride and as the dihydrate form are blue to bluish-green tetragonal rhombododecahedral crystals. During purification, the fraction was neutralized with ammonium hydroxide and allowed to form by slow evaporation indicating that the fraction probably contained some copper(II) chloride that reacted to form these crystals upon evaporation. Based upon all this, the X-ray structure solution was not completed. SEM/EDX analysis was performed on the crystal and verified the presence of copper and chlorine in the crystal.

Clear needle-like plates were also grown from the yellow solution containing peak 8. One of these was selected and mounted on a glass fiber for examination by X-ray. The crystal diffracted strongly and gave a Monoclinic C lattice with cell constants a=6.2779(6)Å, b=15.2008(16)Å, c=5.6762(6)Å, β=114.095(9)°, and a volume of 494.5(2)Å$^3$. Based upon a Z=8, this volume size suggests only about 3 or 4 non-hydrogen atoms in the asymmetric unit. Thus, it is believed that the molecule is a simple salt or possesses internal symmetry. The data set was collected and solved in space group #5 (C2) based upon the systematic absences of the data. With Z=4 the structure was refined to R factors of 6.8 and 7.0 percent where the identity of the material was determined to be the mineral gypsum ($CaSO_4 \cdot 2H_2O$). A comparison to the ICDD database shows gypsum (Card #21-0816) matches the unit cell and lattice found in our analysis. SEM/EDX analysis was run on the crystals and showed the presence of calcium, sulfur, and oxygen in the crystal. Gypsum was used as an excipient in the manufacture of Premarin®, and its detection here demonstrates the retention and continual leaching of the excipients by the HPLC column during the chromatographic analysis discussed earlier.

Yellow needle-like crystals were grown from the solution containing peak 8. A crystal was selected and mounted on a glass fiber for X-ray analysis. The crystal diffracted well and gave an Orthorhombic P lattice with cell constants a=18.483(5)Å, b=11.536(1)Å, c=11.440(2)Å, and a volume of 2439(1)Å$^3$. Based upon the volume, the molecule is believed to contain about 33 non-hydrogen atoms in the asymmetric unit if it is an acentric space group and about 16–17 non-hydrogen atoms if it is centric. A search of the ICDD database did not reveal any structures with similar cell constants. The data set was collected and based upon the systematic absences, the space group #51 (Pnna) was selected. The structure was refined to R factors of 6.8 and 7.7 percent and revealed that the molecule sat on a special position (2-fold axis) such that only one-half of the molecule needed to be found and refined. The final structure was shown to be a tertiary butyl amine of the general formula [NBu$_4$][MCl$_4$], where M is a first row transition element in a +3 oxidation state, and is possibly Fe. It appears this complex was formed from the interaction of the mobile phase ion-pairing agent with a metal salt. Since this was not a compound of interest the structure delineation was stopped at this point.

Chromatographic UV analysis during the LC-MS analysis shows a single large peak for this fraction. However, in this instance, examination of the ESI-MS data recorded throughout the chromatogram did not reveal any significant ion that could be assigned to the UV response. A number of weak signals throughout the run were detected but these were polymeric ethoxylates (from the PEG excipient) and were not consistent with the major UV peak. This single major peak in the LC-MS was run under negative ion FAB-MS and showed a possible very weak, sample related molecular ion (M−H)$^{31}$ at m/z 377. Positive ion FAB showed a weak sample related molecular ion (M+Na)$^+$ at m/z 401. Negative ion ESI-MS showed a weak response with high background including the one indicated in FAB-MS analysis at m/z 377. Analysis by ESI-MS/MS was not possible since the ESI-MS spectrum did not reveal a molecular ion. The conclusions of these studies indicated a molecular mass of 378Da. Further analyses were performed to confirm and verify any of these results. To improve sensitivity for the MS analyses, the single peak was collected from the LC-MS and lyophilized to concentrate it for use in subsequent analyses. The negative ion ESI-MS spectrum showed a possible molecular ion (M−H)$^-$ at m/z 371. Positive ion ESI-MS showed a possible molecular ion (M+H)$^+$ at m/z 503 and the corresponding sodium, potassium, and cesium adducts at m/z 525, 541, and 635, respectively. However, previous MS work with this fragment indicated that the above adducts were due to the polymeric ethoxylates from the formulation. The negative ion ESI-MS/MS spectrum was obtained on the parent ion (m/z 371) and showed daughter ions at only m/z 80 and 97 that are consistent with a sulfated moiety. These results suggest a sulfated species with a molecular weight of 372 Da. This result was questioned to some extent since previous HPLC analyses had indicated this peak was non-sulfated and the sample generated an inherently poor response to the MS methods. The presence of other minor impurities may actually bind or mask peak 8.

Based upon the previous ion-pairing experiments and diode array spectral information from HPLC analysis, peak 8 was suspected to be an aromatic carboxylic acid. This information was used to try to find an organic carboxylic acid that matched the specific retention time and diode array. Benzoic acid, sodium salt, was readily available from Chem Service and was analyzed by HPLC. Overlays of the chromatograms and the diode array spectra of the benzoic acid and Premarin® showed matching peak shape and retention times and identical diode array spectra for the peaks confirming the identity of peak 8 as benzoic acid. According to *The Merck Index*, benzoic acid occurs in the urine of vertebrates.

Peak 1 Investigation

Peak 1 was extracted from the dry rotary evaporator mixture of buffer and compound using ethanol. This solution was then concentrated on the rotary evaporator to produce a yellow viscous oil. Portions of this fraction were set aside to attempt crystallization and for use in other physical testing to characterize the material.

After finding and characterizing hippuric acid (peak 4) in Premarin® as described above, work was carried out to evaluate other organic compounds know to be present in urine. Methylhippuric acid (o-, m-, and p-), mandelic acid, and creatinine were injected onto the chromatographic system. Of these, creatinine gave a peak that conformed to a peak detected in Premarin®. According to *The Merck Index*, creatinine is a normal constituent of urine. Overlays of the chromatograms and the diode array spectra of the standard and an injection of Premarin® showed matching retention times and identical diode array spectra for the peaks confirming the identity of peak 1 as Creatinine.

Investigation of Other Peaks

Peak 9 was extracted from the dry rotary evaporator mixture using ethanol and concentrated on the rotary evaporator to produce a yellow viscous oil. This was set aside to crystallize and after several days, a single small clear plate of dimensions 0.01×0.04×0.06 mm formed. It was subsequently mounted on a glass fiber for X-ray analysis. The crystal diffracted well and a search generated a Monoclinic P lattice with cell constants a=1.273(1)Å, b=11.168(2)Å, c=8.556(1)Å, β=101.24(1)° and a volume of 1056.5(5)Å³. Based upon the volume, a centric space group would suggest about 14 non-hydrogen atoms in the asymmetric unit, while an acentric space group would suggest about 28 atoms. A search of the ICDD database did not reveal any structures with similar cell constants. The data set was collected and based upon systematic absences, the centric space group #14 (P2₁/c) was selected. With Z=2, the structure was refined to R factors of 4.2 and 4.2%. The molecule possessed internal symmetry and sat on a special position (center of inversion) thus, only one-half of the atoms in the structure needed to be found and refined. The final structure was shown to be that of an octahedral copper(II) complex. The complex exhibited four water molecules in a planar arrangement of the octahedron with two organic molecules (:N═C(CH₃)—C₆H₄—SO₃) coordinated through the nitrogen atoms occupying the caps of the octahedron. To confirm the identity of the material, the crystal was dissolved in mobile phase and injected into the HPLC system. The retention time of the peak generated was not close to the retention time of peak 9 indicating the copper complex was probably formed during crystallization from some copper(II) salt and the organic moiety. Peak 9 may be the uncoordinated sulfated organic moiety.

Additional Investigations

Compositional information submitted by Wyeth-Ayerst to the FDA (letters dated January 14, February 13, and Mar. 24, 1997) was obtained via the Freedom of Information Act (FOIA). These data were generated by GC analysis on acid-hydrolyzed [1% trifluoroacetic acid (TFA) in dioxane] Conjugated Estrogens, USP to determine the steroidal components present. It was reported that Conjugated Estrogens, USP is a mixture of 17 estrogen sulfates, three progestins, four progestin sulfates, and four androgens. In addition to the ten USP-defined sulfated estrogens, Wyeth-Ayerst reported the presence of:

Seven estrogens:
1. 17α-Dihydro-Δ⁸,⁹-dehydroestrone sulfate, sodium salt
2. 17β-Dihydro-Δ⁸,⁹-dehydroestrone sulfate, sodium salt
3. 1,3,5(10)-Estratrien-2,3-diol-17-one-3-sulfate, sodium salt
4. 1,3,5(10)-Estratrien-2,3-diol-17-one-2-methyl ether-3-sulfate, sodium salt
5. 5,7,9(10)-Estratrien-3 β, 17β-diol-3-sulfate, sodium salt
6. 5,7,9(10)-Estratrien-3β-ol-17-one-3-sulfate, sodium salt
7. 5(10),7-Estradiene-3β-ol-17-one-3-sulfate, sodium salt Seven progestins:
1. 5α-Pregnan-3β,20β-diol-3-sulfate, sodium salt
2. 5α-Pregnan-3β,20β-diol-20-sulfate, sodium salt
3. 5α-Pregnan-3β-ol-20-one
4. 5α-Pregnan-3 β,20β-diol-disulfate, disodium salt
5. 5α-Preg-16-nen-3β-ol-20-one
6. 5α-Pregnan-3β,16α,20β-triol
7. Preg-4-nen-20-ol-3-one-20-sulfate, sodium salt And four androgens:
1. 5α-Androstan-3β-ol-16-one
2. 5α-Androstan-3β,16α-diol
3. 5α-Androstan-3β,16β-diol
4. 5α-Androstan-3β,17α-diol These data were surprising, as it is not expected that hydrophobic progestational and androgenic compounds would be present in the water-soluble extracts of equine urine. Although the progestins and androgens are, by definition, not water-soluble estrogens, available samples and related compounds were obtained for use as qualitative standards to substantiate the Wyeth-Ayerst data. Table 4 lists a tabulation of the compounds purchased for this investigation.

TABLE 4

Estrogens 1,3,5(10)-Estratrien-3,17β-diol-3,12 disulfate sodium
1,3,5(10)-Estratrien-3,17β-diol-17-sulfate sodium
1,3,5(10)-Estratrien-2,3,17β-triol
1,3,5(10)-Estratrien-2,3,17β-triol-2-methyl ether
1,3,5(10)-Estratrien-2,3-diol-17-one-2-methyl ether
1,3,5(10)-Estratrien-3-ol-17-one-3-methyl ether
1,3,5(10)-Estratrien-3,17β-diol-3-methyl ether
1,3,5(10)-Estratrien-2,3,17β-triol-2,3-dimethyl ether
1,3,5(10)-Estratrien-3,16α,17α-triol
1,3,5(10)-Estratrien-3,16α,17β-triol
1,3,5(10)-Estratrien-3,16α,17β-triol-3-sulfate sodium
1,3,5(10)-Estratrien-3,16α,17β-triol-16,17 disulfate disodium
1,3,5(10),6-Estratetraen-3-ol-17-one
1,3,5(10),6-Estratetraen-3,17β-diol Androgens 5α-Androstan-3β,16α-diol
5α-Androstan-3β,16β-diol
5α-Androstan-3β,17β-diol
5α-Androstan-3β-ol-16-one
5α-Androstan-3α-ol-17-one-3-sulfate sodium Progestins 5α-Pregnan-3β,20α-diol
5α-Pregnan-3β,20β-diol
5α-Pregnan-3β-ol-20-one
4-Pregnen-20β-ol-3-one
16,5α-Pregnen-3β-ol-20-one The presence of the 17α- and 17β-hydroxy derivatives of Δ⁸,⁹-dehydroestrone sulfate (estrogens #1 and #2) have been confirmed and are described above.

Evaluation of estrogen #3 was performed using an injection of 1,3,5(10)-estratrien-2,3,17β-triol. This injection exhibited an HPLC chromatogram that contained a single peak at 9.945 minutes. When compared to a Premarin® injection from that same run this peak generated an RRT value of 0.584 and was not detected in Premarin®. Based on RRT relationships described above, estrogen #3 (sodium 1,3,5(10)-estratrien-2,3-diol-17-one-3-sulfate) which is the sulfated 17-one derivative of 1,3,5(10)-estratrien-2,3-diol-17β-triol, was predicted to have an RRT of 0.533. When this region was examined, an unidentified peak was present at an RRT value of 0.515. An overlay of the diode array spectra of the peak at an RRT of 0.515 revealed a similar diode array spectrum with the expected bathochromic shift due to the added -OH substitution at the 2 position of the aromatic phenolic ring. When the diode array spectrum was compared to the non-sulfated 2,3,17β-triol, a small bathochromic shift similar to what was seen for the desulfonation of estrone was observed. These data presented evidence that the identity of the peak at an RRT value of 0.515 was the compound 1,3,5(10)-estratrien-2,3-diol-17-one-3-sulfate (estrogen #3), which is one t5 of the known oxidative metabolites of estrone. The phenolic A ring substitution present on this compound is known to impair binding to estrogen receptors; this compound is not considered to contribute significantly to estrogenic activity.

An authentic standard of estrogen #4 was not commercially available, but a standard of 1,3,5(10)-estratrien-2,3- diol-17-one-2-methyl ether (non-sulfated 20 derivative of estrogen #4) was injected to evaluate the possible presence of estrogen #4 in Premarin®. Comparison of the retention time of the standard at 37.652 minutes to that of a Premarin® injection from the same run generated an RRT value of 2.171. The predicted RRT value for estrogen #4 of 1.241 was derived from the comparison of the RRT relationship for non-sulfated estrone (RRT=1.750) to the non-sulfated standard (RRT=2.171) and relating that ratio to the estrone sulfate peak (RRT=1.000). When this region of the Premarin® chromatogram was examined no peaks greater than 0.1% were detected. These results indicate that estrogen #4 is not present in Premarin®. Estrogen #4 contains a phenolic A ring substitution which, like estrogen #3, is known to obviate binding to estrogen-receptors. The presence or absence of these estrogens should not contribute significantly to estrogenic activity in Conjugated Estrogens, USP.

Samples of related compounds for the last three estrogens (#5–7) reported by Wyeth-Ayerst were not commercially available. These three compounds lack the fundamental structural attributes required for estrogenic activity (the phenolic A ring). All three compounds contain saturated A rings and varying degrees of unsaturation of the B ring. Without authentic standards, the prediction and location of these compounds is difficult. Based upon general knowledge of the hydrophobic interactions on the reversed phase HPLC system, estrogens #5–7 would be expected to occur in the region after estrone sulfate. However, this region shows no unidentified peaks greater than 0.1%. Even when the organic level of the mobile phase was increased in an attempt to shorten retention times and sharpen any late eluting peaks, no additional peaks were detected. A peak for estrogen #7 should have been observed based upon the amount Wyeth-Ayerst reported present from the GC acid hydrolysis experiments. In their report, Wyeth-Ayerst claimed that the 10 estrogens compose about 13.3% by weight of the drug substance, and that estrogen #7 (estradiene) is the fourth largest estrogen present. A peak of this magnitude should have been detected by the chromatographic methods if it was present. The presence or absence of these non-estrogenic compounds are not expected to impact the estrogenic activity of Premarinn (conjugated estrogens, USP).

Authentic standards or derivatives for all but one of the Wyeth-Ayerst reported progestins and androgens were commercially available. Of those 11 reported steroids, authentic standards of progestins #3 and #5 and androgens #1, #2, #3 were obtained. Progestins #1, #2, #4 and #7 were obtained as the non-sulfated derivatives and androgen #4 was obtained as the 17β-derivative of the reported compound. The peaks detected from the injections of these 10 standards did not match any peaks or, in the case of the derivatives, any predicted peaks in Premarin®. However, these compounds are chemically very hydrophobic with poor chromophores, and in the HPLC chromatographic system appeared as very broad peaks at long retention times limiting the ability to accurately detect them.

To improve the chromatography, the organic portion of the mobile phase was increased, which shortened the retention times and sharpened the peaks. In the development of the new HPLC method, authentic standards of progestins #3 and #5 and androgen #1 had the strongest chromophores and were selected for use. To confirm the quality of the commercial standards purchased, the identities of progestin #3 and androgen #3 were verified by single crystal X-ray diffraction. Crystals were grown of both compounds and were found to crystallize in acentric space group #4 ($P2_1$). Each of the compounds contained unit cells with two unique molecules in the asymmetric unit. The structures were refined and confirmed the identities of the compounds. Progestin #5 was investigated using HPLC by altering the mobile phase composition to a 40:60 ratio of organic:aqueous. The standard was prepared to represent about a 1% level in Premarin® and was observed as a small distinct peak at a retention time of about 45.85 minutes. Examination of an overlay of this chromatogram with a Premarin® tablet injection under the same conditions did not reveal any corresponding peak in Premarin®. Progestin #3 was investigated using HPLC by changing the UV detection to 205 nm and altering the mobile phase composition to a 50:50 ratio of organic:aqueous. The standard was prepared to represent about a 1% level in Premarin® and was observed as a small distinct peak at a retention time of about 15.11 minutes. Examination of an overlay of this chromatogram with a Premarin® tablet injection under the same conditions did not reveal any corresponding peak in Premarin®. Likewise, androgen #1 was investigated using HPLC by changing the UV detection to 205 nm and altering the mobile phase to a 40:60 ratio of organic:aqueous. The standard was prepared to represent about a 1% level in Premarin® and at that level no distinct peak was detected. The standard level was increased to 5% where it was observed as a small distinct peak at a retention time of about 15.24 minutes. An overlay of this chromatogram with a Premarin® tablet injection under the same conditions did not reveal any corresponding peak in Premarin® at the same retention time, but other peaks in that region made absolute detection difficult. Based upon these results it did not appear that the compounds tested were detected in Premarin® tablet injections.

A search of the available literature on the Internet and a keyword search of *The Merck Index* (twelfth edition) on CD-ROM were undertaken to review the information available about the known chemical components present in urine. Additionally, chemical catalogues were searched for suspected and chemically similar steroidal based compounds. Any compounds that were found and commercially available from these searches were purchased and investigated using the HPLC Chromatographic Assay Method described above. The compounds were compared to Premarin® to check for the presence of the component at the specific RRT and if a match was found, the diode array spectra were overlaid and examined. Steroidal peaks injected were also used to examine the predicted regions for related compounds (sulfated versus non-sulfated, ketone versus hydroxyl, etc.) based upon the patterns developed for the conjugated estrogens. Table 4 above and Table 5 list some of the extensive list of compounds examined.

TABLE 5

Other Possible Compounds in Urine
Examined for Comparison to Premarin ®
Peaks o-Methylhippuric acid
m-Methylhippuric acid
p-Methylhippuric acid
d,l-Mandelic acid
4-Pyridoxid acid
Indole
Biopterin
Uric acid
4-Picoline
d-Glucoronic acid
Equol The retention times and diode array spectra of injections of these compounds relative to the known conjugated estrogens were important to develop knowledge about the effect of substitution on the steroidal ring system. However, none of the compounds tested or their predicted derivatives exhibited a good match to the peaks present in Premarin®.

Estriol (1,3,5(10)-estratrien-3,16α,17β-triol), which according to *The Merck Index* is usually the predominant estrogenic metabolite in urine, was expected to be present. Samples of both the sulfated and non-sulfated forms of estriol were injected in the HPLC system. The sample peaks in the chromatograms matched up well with the retention times of unknowns in Premarin® at RRT values of 0.121 and 0.174 for the sulfated and non-sulfated forms. However, when the diode array spectra were overlaid, it was determined that neither of the pairs of two peaks were the same components and that estriol sulfate and estriol were not present in Premarin® tablets.

Summary of Peak Investigations from Premarin® Tablets

Investigations of the collected fractions of the peaks revealed that during the HPLC chromatographic runs Premarin® tablets seem to continually leach excipients and inorganic metallic salts into the system causing an increase in the baseline. Excipients, such as the polyethylene glycol and wax, caused the individual peak solutions to be yellow viscous oils, making analytical work and elucidation of the structural identities more difficult. However, the characterization of the five largest peaks was completed and revealed that they were simple organic compounds known to be present in urine. Additional literature searches and work with related samples and standards allowed for the characterization of the peak at RRT of 0.515. This left only fourteen peaks unidentified above 0.1%. Of these seven are $\leq 0.5\%$, four are $>0.5$ and $\leq 1.0\%$, and only three are $>1.0$ and $\leq 2.0\%$.

Investigation of Premarin® Intravenous

Three current Premarin® intravenous lots were also examined by the same HPLC method used for Premarin® tablets. Premarin® intravenous was chosen since it contains the same Conjugated Estrogens, USP, drug substance, as Premarin® tablets, but does not contain the excipients that had caused leaching problems in the chromatography for tablet samples. The chromatograms were examined to investigate the consistency of the Conjugated Estrogens, USP, drug substance from product to product. The three Premarin® intravenous lots were examined by the HPLC Chromatographic Assay Method described above. The three lots yielded similar chromatographic patterns. An overlay of one of the intravenous lots with a Premarin® tablet lot, however, showed substantial differences in the peak patterns observed in the first seven minutes. None of the large peaks observed in the tablet chromatograms represent components of Conjugated Estrogens, USP. The newest lot of Premarin® Intravenous (Lot 3980226) contained 15 peaks>0.1% in addition to the ten USP-defined conjugated estrogens. The identities of the peaks from chromatograms of Premarin® intravenous were confirmed by comparison of the diode array spectra to the corresponding RRT peaks from chromatograms of Premarin® tablets. Comparison of the unidentified Premarin® tablet peaks and all of the Premarin® Intravenous peaks revealed only six of the 15 peaks which were not previously identified or eliminated (RRT values of 0.268, 0.284, 0.338, 0.387, 0.601, and 0.738). Examination of the levels of these six peaks in the two products revealed that all of these unknown component levels varied far beyond the 50% variation criteria expected for controlled components. Elimination of these uncontrolled peaks as inconsistent leaves no peaks uncharacterized in Premarin®. Therefore, the essential estrogenic compounds in Premarin® were determined to be salts of conjugated estrone, conjugated equilin, conjugated $\Delta^{8,9}$-dehydroestrone, conjugated 17α-estradiol, conjugated 17α-dihydroequilin, conjugated 17β-dihydroequilin, conjugated 17β-estradiol, conjugated equilenin, conjugated 17α-dihydroequilenin, and conjugated 17β-dihydroequilenin.

Example 2

HPLC Assay Method

A. Instruments and Equipment
  1. HP 1100 HPLC system equipped with temperature controlled column compartment or equivalent for Separation A
  2. An HPLC system with a variable wavelength UV detector for Separation B
  3. Appropriate analytical balance and microbalance
  4. Appropriate pH Meter
  5. Millipore 0.45 μm HVLP 45 mm membrane filters
  6. Titan 0.45 μm PTFE filters with 1 μm pre-filter
  7. Supelco $C_{18}$, 3 μm particle size, 15 cm×4.6 mm column
  8. Supelco $C_{18}$, 3 μm particle size, 20 cm×4.6 mm column B. Reagents, Standards And Media
  1. 10-Component conjugated estrogens drug substance tested and assigned standard purities
  2. Estrone reference standard, USP or client specified
  3. Equilin reference standard, USP or client specified
  4. 17α-Dihydroequilin reference standard, USP or client specified
  5. Potassium phosphate monobasic, reagent grade
  6. Milli-Q water or equivalent
  7. 85% Phosphoric acid, reagent grade
  8. Acetonitrile, HPLC grade
  9. Methanol, HPLC grade
  10. Suitable pH buffers
  11. Tetrabutylammonium hydroxide (TBAH), 0.4 M±0.02 M (aqueous) titrant, reagent grade C. Suggested Sample Size
  10 tablets of each sample D. Solutions Preparation As these chromatographic methods may be sensitive to the composition of the mobile phase, the analysis may be improved if care is taken during preparation of the diluents and the mobile phase.

A 50 mM phosphate buffer solution may be prepared by dissolving approximately 40.8 g of potassium phosphate monobasic in 6000 mL of water and filtering the resulting solution through an HVLP 0.45 μm filter.

An organic diluent containing a solution of acetonitrile and methanol with a volumetric ratio of 24.5:4.5 may be prepared by combining 1225 mL of acetonitrile and 225 mL of methanol, mixing well, and letting the solution equilibrate to room temperature.

An aqueous diluent containing the phosphate buffer and 0.4 M TBAH solution with a volumetric ratio of 71:0.17 may be prepared by combining 3550 mL of the phosphate buffer and 8.5 mL of 0.4 M TBAH solution and mixing well. The mobile phase for separation A includes a solution of organic diluent and aqueous diluent with a volumetric ratio of 29:71. This mobile phase may be prepared by combining 1160 mL of organic diluent and 2840 mL of aqueous diluent, mixing well, and degassing the resulting solution.

The mobile phase for separation B includes a solution of acetonitrile, methanol, phosphate buffer, and 0.4 M TBAH solution with a volumetric ratio of 6:38:56:0.4. This mobile phase may be prepared by first combining 2240 mL of phosphate buffer with 16 mL of 0.4 M TBAH solution, and the adjusting the pH of the resulting solution to 3.0±0.1 with 85% phosphoric acid. To this mixture, 240 mL of acetonitrile and 1520 mL of methanol are added. The resulting solution is then mixed well and degassed.

A blank injection solution may be prepared using the same diluents that are used to prepare samples. The blank injection solution may be prepared by adding 29 mL of the organic diluent into a 100 mL volumetric flask, diluting the organic diluent to volume with aqueous diluent, and mixing well.

E. Standards Preparation

A standard solution containing about 0.03 mg/mL of conjugated estrogens may be prepared by weighing approximately 160 mg of the 10-component conjugated estrogens drug substance (label claim 37.5 $\mu$g/mg) and transferring the weighed drug substance to a 200 mL volumetric flask. A volume of 100 mL of Mobile Phase A is added to the flask and the flask is mechanically shaken for 15 minutes. The resulting solution is then diluted to volume with Mobile Phase A and mixed well. The standard solution may be stable for 13 days at ambient conditions. A portion of the solution is filtered through a 0.45 $\mu$m PTFE filter with a 1 $\mu$m pre-filter, discarding the first 3 mL.

A Sensitivity Solution A containing about 0.048 $\mu$g/mL solution (equivalent to 0.1% label claim relative to the total conjugated estrogens) of conjugated estrogens in Mobile Phase A may be prepared. A 2.0 mL volume of the standard preparation is pipetted into a 100 mL volumetric flask. The standard solution is then diluted to volume with Mobile Phase A and mixed well. 2.0 mL of the resulting solution is then pipetted into a 25 mL volumetric flask, diluted to volume with Mobile Phase A, and mixed well. The Sensitivity Solution A may be stable for 4 days at ambient conditions.

A stock free steroids solution containing a 0.2 mg/mL solution of estrone RS, equilin RS, and 17$\alpha$-dihydroequilin RS in methanol may be prepared by weighing approximately 10 mg of 17$\alpha$-dihydroequilin, equilin, and estrone and quantitatively transferring these into a 50 mL volumetric flask. The flask is filled to approximate half-volume with methanol. The flask is then sonicated until the solids have dissolved (approximately 15 minutes). The solution is allowed to cool to room temperature, then diluted to volume with methanol and mixed well. The stock free steroids solution may be considered suitable throughout the period that the qualitative profile for the peaks of interest is maintained. It is preferably stored in a refrigerator.

A resolution solution containing about 0.03 mg/mL of 10-component conjugated estrogens and approximately 0.006 mg/mL each of 17$\alpha$-dihydroequilin, equilin, and estrone may be prepared by weighing approximately 80 mg of 10-component conjugated estrogens drug substance (label claim 37.5 $\mu$g/mg) and transferring the resulting solution to a 100 mL volumetric flask. A 50 mL volume of Mobile Phase A is then added to the flask and the flask is mechanically shaken for 15 minutes. 3.0 mL of stock free steroids solution is added to the flask. The resulting solution is diluted to volume with Mobile Phase A and mixed well. A portion of the solution is filtered through a 0.45 $\mu$m PTFE filter with a 1 $\mu$m pre-filter, discarding the first 3 mL. The resolution solution preferably is not for quantitation purposes. It is preferably stored in the refrigerator and is suitable to use throughout the period that the qualitative profile for the peaks of interest is maintained.

F. Sample Preparation

Samples to be analyzed may be prepared. For Premarin® tablets, about 10–20 tablets are washed in water to remove the outer coating then blown to dryness under a nitrogen purge. The tablets are then ground in a grinder at 450 RPM for 1 minute.

When using 0.3 mg tablets to prepare the sample solution, ten tablets (for Premarin®, an amount of washed and ground tablets equivalent to 10 average tablet weight (ATW)) are placed in a 100 mL volumetric flask. A 29 mL volume of organic diluent is added and the flask is mechanically shaken for 10 minutes. About 50 mL of aqueous diluent is added to the resulting solution and the flask is again mechanically shaken for 10 minutes. The resulting solution is then diluted to volume with aqueous diluent and mixed. A portion of the solution is filtered through a 0.45 $\mu$m PTFE filter with a 1 $\mu$m pre-filter, discarding the first 3 mL. To prevent evaporation, the filtrate is preferably placed promptly into the injection vials.

When using 0.625 mg tablets to prepared the sample solution, ten tablets (for Premarin®, an amount of washed and ground tablets equivalent to 10 average tablet weight (ATW)) are placed in a 200 mL volumetric flask. A 58 mL volume of organic diluent is added to the flask and the flask is mechanically shaken for 10 minutes. About 100 mL of aqueous diluent is added to the resulting solution and the flask is once again mechanically shaken for 10 minutes. The resulting solution is diluted to volume with aqueous diluent and mixed. A portion of the solution is filtered through a 0.45 $\mu$m PTFE filter with a 1 $\mu$m pre-filter, discarding the first 3 mL.

When preparing a sample solution using 1.25 mg tablets, ten tablets (for Premarin®, an amount of washed and ground tablets equivalent to 10 average tablet weight (ATW)) are placed in a 400 mL volumetric flask. A 116 mL volume of organic diluent is added to the flask and the flask is mechanically shaken for 10 minutes. About 200 mL of aqueous diluent is then added to the resulting solution and the flask is once again mechanically shaken for 10 minutes. The resulting solution is diluted to volume with aqueous diluent and mixed. A portion of the solution is filtered through a 0.45 $\mu$m PTFE filter with a 1 $\mu$m pre-filter, discarding the first 3 mL. To prevent evaporation, the filtrate is preferably placed promptly in the injection vials. Sample solutions for tablets may be considered stable up to 37 hours at ambient conditions.

G. Instrumental Conditions

Separation A

Column: Supelco $C_{18}$, 3 $\mu$m particle size, 15 cm×4.6 mm

Column temperature: 17° C., maintained with a column cooler

Detection: UV, 220 nm

Mobile phase: Mobile phase A

Flow rate: 1.5 mL/minute

Equilibration time: allow 30 minutes before first injection with flow rate of 1.5 mL/minute Injection volume: 120 $\mu$L (a seat capillary of 400 $\mu$L must be added to autosampler to inject over 100 $\mu$L)

Quantitation: Peak areas

Approximate run times: Standard-45 min; resolution-55 min; sample-65 min

TABLE 6

| Component | Abbreviation | RRT |
|---|---|---|
| 17β-dihydroequilenin sulfate | BDHENS | 0.40 |
| 17β-dihydroequilin sulfate | BDHES | 0.47 |
| 17α-dihydroequilenin sulfate | ADHENS | 0.54 |
| 17β-estradiol sulfate | BESDS | 0.56 |
| 17α-dihydroequilin sulfate | ADHES | 0.65 |
| 17α-estradiol sulfate | AESDS | 0.78 |
| equilenin sulfate | EQNS | 0.81 |
| Equilin sulfate/$\Delta^{8,9}$-dehydroestrone sulfate | EQD8 | 0.89 |
| Estrone sulfate | ESTS | 1.00 |
| 17α-dihydroequilin | ADHE | 1.17 |
| equilin | EQU | 1.61 |
| estrone | EST | 1.80 |

Separation B

Column: Supelco $C1_8$, 3 μm particle size, 20 cm×4.6 mm
  Column temperature: 30° C., maintained with a column heater
  Detection: UV, 220 nm
  Mobile phase: Mobile phase B
  Flow rate: 1.0 mL/minute
  Equilibration time: allow 30 minutes before first injection with flow rate of 1.0 mL/minute
  Injection volume: 40 μL
  Quantitation: Peak areas
  Approximate run time: Sample/standard-45 min; resolution-70 min

TABLE 7

| Component | Abbreviation | RRT |
|---|---|---|
| $\Delta^{8,9}$-dehydroestrone sulfate | D89DS | 0.96 |
| equilin sulfate | EQUS | 1.00 |
| 17β-estradiol sulfate | BESDS | 1.05 |

An example of a chromatographic procedure is as follows: equal volumes of the standard and sample preparation are injected into the desired HPLC system. Chromatographic separation B is used for identifying and quantifying the equilin sulfate and $\Delta^{8,9}$-dehydroestrone sulfate peaks. Chromatographic separation B is used for identifying and quantifying the peaks of the remaining estrogens and unknown impurities.

Example 3

Mobile Phase Robustness-Separation A

The mobile phase robustness of Separation A, described above in Example 2, was investigated by making slight deliberate changes to the mobile phase composition. Variations to the amount of acetonitrile in the mobile phase (+/−1%), to the amount of methanol (+/−1% absolute value), to the amount of tetrabutyl ammonium hydroxide (TBAH) (+/−10% absolute value), to the buffer pH (+/−0.2 units), and to the concentration of the buffer (+/−10%) were made. One injection of the resolution solution, described above in Example 2, and three replicate injections of a sample preparation of the 0.3 mg formulation, described above in Example 2, were made using the different mobile phase compositions. In addition, one injection of a placebo solution for the 0.3 mg formulation (Lot 00532-006) and injections of two degraded sample solutions (Lot 00484-066, treated with 3% hydrogen peroxide for 5 minutes and heated for 24 hours at 80° C.) were made using each of the different mobile phase compositions. The following were calculated and are reported in Table 8 below:

1. Resolution between 17α-estradiol sulfate (AEDS) and equilenin sulfate (EQNS).
2. Resolution between equilin sulfate/$\Delta^{8,9}$-dehydroestrone sulfate (EQD8) and estrone sulfate (ESTS).
3. Resolution between estrone sulfate (ESTS) and 17α-dihydroequilin (ADHE).
4. The percent relative standard deviation (RSDs) for 17α-dihydroequilin sulfate (ADHES) and ESTS from the triplicate sample injections.
5. The mean tailing factors for ADHES and ESTS in the sample injections.

All separation requirements (i.e. resolution between peaks, tailing factor, and reproducibility of multiple injections) for the TBAH variations, the buffer concentration variations, and the pH variations were met.

For an injection of the resolution solution using a mobile phase containing 24.5% acetonitrile, the resolution between AESDS and EQNS failed the separation requirements; however, the test procedure allows for a variation in the column temperature to improve this separation. Decreasing the temperature from 20 to 17° C. improved the separation, and the separation requirements were met. For an injection of the resolution solution using a mobile phase containing 26.5% acetonitrile, the shoulder for the BESDS peak on the ADHENS peak was not distinctive; therefore, a new mobile phase was prepared containing 26% acetonitrile and the shoulder was clearly visible.

For an injection of the resolution solution using a mobile phase containing 3% methanol, the resolution between ESTS and ADHE did not meet the separation requirements. The test procedure allows for the tetrabutyl ammonium hydroxide concentration of the mobile phase to be lowered to improve the separation between ESTS and ADHE. For every liter of mobile phase, 100 mL of a solution with the composition (25.5:3:71.5) acetonitrile:methanol:water was added. Following this adjustment, all separation requirements were met. For an injection of the resolution solution using a mobile phase containing 5% methanol, all separation requirements were met.

Injections of the placebo solution using the different mobile phase compositions showed no differences in the chromatograms. Injections of the two degraded sample solutions showed no peaks that interfered with the conjugated estrogens.

The method was shown robust within the ranges listed. However, the mobile phase has been shown sensitive to variations in methanol, acetonitrile, and tetrabutylammoniumhydroxide. Thus, care should be used when preparing the mobile phase. The studies have shown that adjustments may be made to the mobile phase that are suitable for improving separation.

TABLE 8

| Condition | Resolution | | | % RSD | | Mean Trailing | |
|---|---|---|---|---|---|---|---|
| | AESDS/ EQNS | EQD8/ ESTS | ESTS/ ADHE | ADHES | ESTS | ADHES | ESTS |
| Control | 1.4 | 3.0 | 2.4 | 0.2 | 0.4 | 1.2 | 1.4 |
| 24.5% ACN | 1.3 | 2.8 | 2.2 | 0.7 | 0.2 | 1.3 | 1.6 |
| 26% ACN | 1.3 | 2.8 | 4.6 | 0.2 | 0.1 | 1.3 | 1.5 |
| 3% MeOH | 1.6 | 2.9 | 2.1 | 1.2 | 0.6 | 1.3 | 1.5 |
| 5% MeOH | 1.1 | 2.9 | 4.7 | 0.1 | 0.1 | 1.2 | 1.5 |
| 0.18% TBAH | 1.2 | 2.9 | 5.9 | 0.2 | 0.1 | 1.3 | 1.5 |
| 0.22% TBAH | 1.3 | 2.8 | 2.6 | 0.3 | 0.3 | 1.3 | 1.5 |
| pH 2.8 Buffer | 1.6 | 3.0 | 3.1 | 0.1 | 0.3 | 1.2 | 1.4 |
| pH 3.2 Buffer | 1.4 | 2.9 | 3.0 | 0.1 | 0.3 | 1.2 | 1.4 |
| 40 mM Buffer | 1.6 | 2.8 | 4.2 | 0.2 | 0.2 | 1.2 | 1.4 |
| 60 mM Buffer | 1.4 | 2.5 | 4.3 | 0.4 | 0.3 | 1.4 | 1.5 |

Example 4

Mobile Phase Robustness-Separation B

Mobile phase robustness studies for Separation B, described above in Example 2, were performed to evaluate the effects of minor deviations in the mobile phase. The variations made to the mobile phase composition are outlined in Table 9 below. One injection of the resolution solution was made and the resolution between the $\Delta^{8,9}$-dehydroestrone sulfate and equilin sulfate (D89DS/EQUS) peaks and the equilin sulfate and 17β-estradiol (EQUS/BESDS) peaks were monitored. Next, two injections of a sample solution of a 0.625 mg formulation (Lot 00426-056, FDL/AASI) were analyzed using each mobile phase. All separation requirements (i.e. resolution between peaks, tailing factor, and reproducibility of multiple injections) were met. The method was robust within the conditions tested, but care should be taken with the mobile phase preparation due to the sensitivity of the resulting chromatography.

TABLE 9

| Condition | Resolution | |
|---|---|---|
| | D89DS/EQUS | EQUS/BESDS |
| per test procedure | 1.8 | 1.7 |
| pH 2.5 Buffer | 1.8 | 1.6 |
| pH 3.5 Buffer | 1.8 | 1.8 |
| 1.4 mM TBAH | 1.7 | 1.5 |
| 1.8 mM TBAH | 1.7 | 1.5 |
| 46:54 Organic:Buffer | 1.6 | 1.7 |
| 42:58 Organic:Buffer | 1.6 | 2.1 |
| 63:377 ACN:MeOH | 1.6 | 1.5 |
| 54:386 ACN:MeOH | 1.7 | 2.1 |

Despite numerous attempts over several decades, the essential estrogenic compounds of Premarin® (conjugated estrogens tablets, USP) have heretofore not been determined. Analytical methods of the present invention may be used to determine, for the first time, the essential estrogenic compounds present in Premarin® (conjugated estrogens tablets, USP). Having unexpectedly been able to determine the essential estrogenic compounds present in Premarin® (conjugated estrogens tablets, USP), compositions of matter and drug products of the present invention may for the first time provide a mixture of synthetic estrogenic compounds where the mixture contains the same essential estrogenic compounds present in Premarin® (conjugated estrogens tablets, USP). As such, compositions of matter and drug products of the present invention may provide a synthetic alternative to naturally derived Premarin® (conjugated estrogens tablets, USP). This may reduce or eliminate what has been perceived to be cruelty to animals while still providing drug products useful in treating diseases and medical conditions such as severe vasomotor symptoms associated with menopause, atrophic vaginitis, osteoporosis, hypoestrogenism due to hypogonadism, castration, or primary ovarian failure, breast cancer in selected persons with metastatic disease, and advanced androgen-dependent carcinoma of the prostate.

The present invention has been described herein with reference to its preferred embodiments. These embodiments do not serve to limit the invention, but are set forth for illustrative purposes. The scope of the invention is defined by the claims that follow.

That which is claimed is:

1. A composition of matter comprising:
   a mixture of estrogenic compounds, wherein said mixture comprises salts of conjugated estrone, conjugated equilin, conjugated $\Delta^{8,9}$-dehyroestrone, conjugated 17α-estradiol, conjugated 17α-dihydroequilin, conjugated 17β-dihydroequilin, conjugated 17β-estradiol, conjugated equilenin, conjugated 17α-dihydroequilin, and conjugated 17β-dihydroequilenin, and wherein said mixture comprises the same essential estrogenic compounds present in naturally derived equine conjugated estrogens;
   wherein said composition of matter is present in a chemically pure form.

2. The composition according to claim 1, wherein the salts are sodium salts.

3. The composition according to claim 1, wherein the conjugates are sulfates.

4. The composition according to claim 1, wherein the mixture further comprises at least one compound selected from the group consisting of equilenin, 17β-dihydroequilenin, 17β-dihydroequilin, 17α-dihydroequilenin, 17β-estradiol, 17α-dihydroequilin, 17α-estradiol, equilin, $\Delta^{8,9}$ ehydroestrone, estrone, 17α-$\Delta^{8,9}$-dehydroestradiol, 17β-$\Delta^{8,9}$-dehydroestradiol, 6-OH 17α-dihydroequilenin, 6-OH equilenin, and the salts of 17α$\Delta^{8,9}$-dehydroestradiol sulfate, 17β-$\Delta^{8,9}$-dehydroestradiol sulfate, 6-OH 17α-dihydroequilenin sulfate, 6-OH 17β-dihydroequilenin sulfate, and 6-OH equilenin sulfate.

5. The composition according to claim 4, wherein the salts of 17α-$\Delta^{8,9}$-dehydroestradiol sulfate, 17β-$\Delta^{8,9}$-dehydroestradiol sulfate, 6-OH 17α-dihydroequilenin sulfate and 6-OH equilenin sulfate are sodium salts.

6. The composition according to claim 1, wherein the mixture comprises:

from about 40 to about 75 percent of the salt of conjugated estrone;

from about 15 to about 40 percent of the salt of conjugated equilin;

from about 2 to about 10 percent of the salt of conjugated $\Delta^{8,9}$-dehydroestrone;

from about 2 to about 10 percent of the salt of conjugated 17α-estradiol;

from about 10 to about 20 percent of the salt of conjugated 17α-dihydroequilin; and from about 0.5 to about 5 percent of the salt of conjugated 17β-dihydroequilin.

7. The composition according to claim 1, wherein the composition further comprises at least one additional pharmaceutically active ingredient.

8. The composition according to claim 7, wherein the at least one additional pharmaceutically active ingredient is selected from the group consisting of androgens, progestins, calcium salts, and vitamin D.

9. A composition of matter comprising:

a mixture of estrogenic compounds, wherein at least one of said estrogenic compounds is a synthetic estrogenic compound, and wherein said mixture comprises the same essential estrogenic compounds present in naturally derived equine conjugated estrogens;

wherein said composition of matter is present in a chemically pure form.

10. The composition according to claim wherein the mixture further comprises at least one compound selected from the group consisting of equilenin, 17β-dihydroequilenin, 17β-dihydroequilin, 17α-dihydroequilenin, 17β-estradiol, 17α-dihydroequilin, 17α-estradiol, equilin, $\Delta^{8,9}$-dehydroestrone, estrone, 17α-$\Delta^{8,9}$-dehydroestradiol, 17β-$\Delta^{8,9}$-dehydroestradiol, 6-OH 17α-dihydroequilenin, 6-OH equilenin, and the salts of 17α$\Delta^{8,9}$-dehydroestradiol sulfate, 17β-$\Delta^{8,9}$-dehydroestradiol sulfate, 6-OH 17α-dihydroequilenin sulfate, 6-OH 17β-dihydroequilenin sulfate, and 6-OH equilenin sulfate.

11. The composition according to claim 10, wherein the salts of 17α-$\Delta^{8,9}$-dehydroestradiol sulfate, 17β-$\Delta^{8,9}$-dehydroestradiol sulfate, 6-OH 17α-dihydroequilenin sulfate and 6-OH equilenin sulfate are sodium salts.

12. The composition according to claim 9, wherein the mixture comprises:

from about 40 to about 75 percent of the salt of conjugated estrone;

from about 15 to, about 40 percent of the salt of conjugated equilin;

from about 2 to about 10 percent of the salt of conjugated $\Delta^{8,9}$-dehydroestrone;

from about 2 to about 10 percent of the salt of conjugated 17α-estradiol;

from about 10 to about 20 percent of the salt of conjugated 17α-dihydroequilin; and from about 0.5 to about 5 percent of the salt of conjugated 17β-dihydroequilin;

wherein the sum of the percentages of the salt of conjugated estrone and the salt of conjugated equilin is between about 70 and about 95 percent of the labeled content, and wherein the ratio of the percentage of the salt of conjugated equilin to the percentage of the salt of conjugated estrone is between about 0.25 and about 0.75.

13. A composition of matter comprising:

a mixture of estrogenic compounds, wherein said mixture comprises the same essential estrogenic compounds present in naturally derived equine conjugated estrogens;

wherein said composition of matter is present in a chemically pure form.

14. The composition according to claim 13, wherein the mixture further comprises at least one compound selected from the group consisting of equilenin, 17β-dihydroequilenin, 17β-dihydroequilin, 17α-dihydroequilenin, 17β-estradiol, 17α-dihydroequilin, 17α-estradiol, equilin, $\Delta^{8,9}$-dehydroestrone, estrone, 17α-$\Delta^{8,9}$-dehydroestradiol, 17β-$\Delta^{8,9}$-dehydroestradiol, 6-OH 17α-dihydroequilenin, 6-OH equilenin, and the salts of 17α$\Delta^{8,9}$-dehydroestradiol sulfate, 17β-$\Delta^{8,9}$-dehydroestradiol sulfate, 6-OH 17α-dihydroequilenin sulfate, 6-OH 17β-dihydroequilenin sulfate, and 6-OH equilenin sulfate.

15. The composition according to claim 14, wherein the salts of 17α-$\Delta^{8,9}$-dehydroestradiol sulfate, 17β-$\Delta^{8,9}$-dehydroestradiol sulfate, 6-OH 17α-dihydroequilenin sulfate and 6-OH equilenin sulfate are sodium salts.

16. The composition according to claim 13, wherein the mixture comprises:

from about 40 to about 75 percent of the salt of conjugated estrone;

from about 15 to about 40 percent of the salt of conjugated equilin;

from about 2 to about 10 percent of the salt of conjugated $\Delta^{8,9}$-dehydroestrone;

from about 2 to about 10 percent of the salt of conjugated 17α-estradiol;

from about 10 to about 20 percent of the salt of conjugated 17α-dihydroequilin; and from about 0.5 to about 5 percent of the salt of conjugated 17β-dihydroequilin;

wherein the sum of the percentages of the salt of conjugated estrone and the salt of conjugated equilin is between about 70 and about 95 percent of the labeled content, and wherein the ratio of the percentage of the salt of conjugated equilin to the percentage of the salt of conjugated estrone is between about 0.25 and about 0.75.

17. A composition of matter comprising:

a mixture of estrogenic compounds, wherein said mixture comprises salts of conjugated estrone, conjugated equilin, conjugated $\Delta^{8,9}$-dehydroestrone, conjugated 17α-estradiol, conjugated 17α-dihydroequilin, conjugated 17β-dihydroequilin, conjugated 17β-estradiol, conjugated equilenin, conjugated 17α-dihydroequilenin, and conjugated 17β-dihydroequilenin, and wherein said mixture comprises the same essential estrogenic compounds present in naturally derived equine conjugated estrogens; and at least one additional pharmaceutically active ingredient selected from the group consisting of androgens, progestins, calcium salts, and vitamin D;

wherein said composition of matter is present in a chemically pure form.

18. The composition according to claim 17, wherein the mixture further comprises at least one compound selected from the group consisting of equilenin, 17β-dihydroequilenin, 17β-dihydroequilin, 17α-dihydroequilenin, 17β-estradiol, 17α-dihydroequilin, 17α-estradiol, equilin, $\Delta^{8,9}$-dehydroestrone, estrone, 17α-$\Delta^{8,9}$- dehydroestradiol, 17β$\Delta^{8,9}$-dehydroestradiol, 6-OH 17α-dihydroequilenin, 6-OH equilenin, and the salts of 17α$\Delta^{8,9}$-dehydroestradiol sulfate, 17β-$\Delta^{8,9}$-dehydroestradiol sulfate, 6-OH 17α-dihydroequilenin sulfate, 6-OH 17β-dihydroequilenin sulfate, and 6-OH equilenin sulfate.

19. The composition according to claim 18, wherein the salts of 17α-$\Delta^{8,9}$-dehydroestradiol sulfate, 17 β-$\Delta^{8,9}$-dehydroestradiol sulfate, 6-OH 17α-dihydroequilenin sulfate, 6-OH 17β-dihydroequilenin sulfate, and 6-OH equilenin sulfate are sodium salts.

20. The composition according to claim 17, wherein the mixture comprises:
   from about 40 to about 75 percent of the salt of conjugated estrone;
   from about 15 to about 40 percent of the salt of conjugated equilin;
   from about 2 to about 10 percent of the salt of conjugated $\Delta^{8,9}$-dehydroestrone;
   from about 2 to about 10 percent of the salt of conjugated 17α-estradiol;
   from about 10 to about 20 percent of the salt of conjugated 17α-dihydroequilin; and
   from about 0.5 to about 5 percent of the salt of conjugated 17β-dihydroequilin;
   wherein the sum of the percentages of the salt of conjugated estrone and the salt of conjugated equilin is between about 70 and about 95 percent of the labeled content of conjugated estrogens, and wherein the ratio of the percentage of the salt of conjugated equilin to the percentage of the salt of conjugated estrone is between about 0.25 and about 0.75.

21. A method of treating mammals in need of treatment for conditions treatable by administration of estrogenic compounds, said method comprising administering an effective amount of a composition of matter according to claim 1.

22. The method according to claim 21, further comprising administering the effective amount of the composition of matter in a continuous and uninterrupted manner.

23. The method according to claim 21, wherein said mammal is in need of treatment for vasomotor symptoms.

24. The method according to claim 21, wherein said mammal is in need of treatment of atrophic vaginitis.

25. The method according to claim 22, wherein said mammal is in need of treatment for osteoporosis.

26. A method for analyzing conjugated estrogen constituents comprising the steps of:
   preparing a solution containing conjugated estrogens, said solution comprising:
      a mixture comprising estrogenic compounds to be analyzed; and
      a mobile phase comprising:
         an organic portion comprising between about 0.1% and about 30% (by volume organic portion)-protic solvent and between about 70% and about 100% (by volume organic portion) polar aprotic solvent; and
         an aqueous portion;
   and analyzing the conjugated estrogens solution utilizing a HPLC system.

27. The method according to claim 26, wherein the mixture comprising estrogen compounds comprises naturally derived equine conjugated estrogens.

28. The method according to claim 26, wherein the protic solvent comprises a lower alkyl alcohol.

29. The method according to claim 28, wherein the lower alkyl alcohol is methanol.

30. The method according to claim 26, wherein the polar aprotic solvent comprises a lower alkyl nitrile.

31. The method according to claim 30, herein the lower alkyl nitrile is acetonitrile.

32. The method according to claim 26, wherein the mobile phase comprises between about 65 and about 80 percent aqueous portion and between about 20 and about 35 percent organic portion.

33. The method according to claim 26, wherein the aqueous portion has a pH of between about 2.5 to about 3.5.

34. The method according to claim 26, wherein the organic portion comprises an ion-pairing agent.

35. The method according to claim 34 wherein the ion-pairing agent has a concentration between about 0.5 to about 2 mM.

36. The method according to claim 34, wherein the ion-pairing agent is tert-butyl ammonium hydroxide.

37. The method according to claim 36, wherein the aqueous portion comprises an ion-pairing agent.

38. The method according to claim 37, wherein the ion-pairing agent has a concentration between about 0.5 to about 2 mM.

39. The method according to claim 37, wherein the ion-pairing agent is tert-butyl ammonium hydroxide.

40. The method according to claim 26, wherein the step of analyzing further comprises the step of fraction collecting at least one of the separated constituents of the conjugated estrogens substance.

41. The method according to claim 40, wherein the step of fraction collecting utilizes a multi-channel fraction collector.

42. The method according to claim 41, wherein the HPLC system comprises a column, and wherein the analyzing step occurs at a column temperature between about 15 and about 35° C.

43. A composition of matter comprising:
   a mixture of estrogenic compounds, wherein said mixture comprises salts of conjugated estrone, conjugated equilin, conjugated $\Delta^{8,9}$-dehydroestrone, conjugated 17α-estradiol, conjugated 17α-dihydroequilin, conjugated 17β-dihydroequilin, conjugated 17β-estradiol, conjugated equilenin, conjugated 17α-dihydroequilenin, and conjugated 17β-dihydroequilenin, and wherein said mixture comprises the same essential estrogenic compounds present in naturally derived equine conjugated estrogens;
   wherein said composition of matter is substantially devoid of a compound selected from the group consisting of indican, sulfated benzyl alcohol, hippuric acid, benzoic acid, and creatinine.

44. A composition of matter comprising:
   a mixture of estrogenic compounds, wherein said mixture comprises salts of conjugated estrone, conjugated equilin, conjugated $\Delta^{8,9}$-dehydroestrone, conjugated 17α-estradiol, conjugated 17α-dihydroequilin, conjugated 17β-dihydroequilin, conjugated 17β-estradiol, conjugated equilenin, conjugated 17α-dihydroequilenin, and conjugated 17β-dihydroequilenin, and wherein said mixture comprises the same essential estrogenic compounds present in naturally derived equine conjugated estrogens;
   wherein said composition of matter is substantially devoid of indican, sulfated benzyl alcohol, hippuric acid, benzoic acid, and creatinine.

* * * * *

UNITED STATES PATENT AND TRADEMARK OFFICE
CERTIFICATE OF CORRECTION

PATENT NO. : 6,855,703 B1
DATED : February 15, 2005
INVENTOR(S) : Hill et al.

It is certified that error appears in the above-identified patent and that said Letters Patent is hereby corrected as shown below:

Column 38,
Line 58, change "ehydroestrone" to -- dehydroestrone --.
Line 61, change "17β-A" to -- 17β-Δ --.

Column 39,
Line 31, change "claim" to -- claim 11 --.
Line 38, change "17αΔ" to -- 17α-Δ --.
Line 50, change "to, about" to -- to about --.

Column 40,
Line 15, change "17αΔ" to -- 17α-Δ --.
Line 20, change "17α-A" to -- 17α-Δ --.

Column 41,
Line 2, change "17αΔ" to -- 17α-Δ --.
Line 54, change "portion)-protic" to -- portion) protic --.

Column 42,
Line 3, change "herein" to -- wherein --.

Signed and Sealed this

Sixteenth Day of August, 2005

JON W. DUDAS
*Director of the United States Patent and Trademark Office*